(12) United States Patent
Natarajan et al.

(10) Patent No.: US 6,288,055 B1
(45) Date of Patent: Sep. 11, 2001

(54) ANALGESIC AGENTS

(75) Inventors: Maya Natarajan, San Diego; Thomas E. Jenkins, La Honda; John H. Griffin, Atherton, all of CA (US)

(73) Assignee: Advanced Medicine, Inc., So. San Francisco, CA (US)

( * ) Notice: Subject to any disclaimer, the term of this patent is extended or adjusted under 35 U.S.C. 154(b) by 0 days.

(21) Appl. No.: 09/499,476

(22) Filed: Feb. 7, 2000

Related U.S. Application Data

(63) Continuation of application No. 09/327,044, filed on Jun. 7, 1999, now abandoned.
(60) Provisional application No. 60/088,466, filed on Jun. 8, 1998, and provisional application No. 60/092,938, filed on Jul. 15, 1998.

(51) Int. Cl.[7] .................. C07D 401/12; A61K 31/44
(52) U.S. Cl. .................. 514/210.2; 514/333; 546/256
(58) Field of Search .................. 514/210.2, 333; 546/256

(56) References Cited

U.S. PATENT DOCUMENTS

| | | | |
|---|---|---|---|
| 5,837,815 | 11/1998 | Lev et al. | 530/350 |
| 5,846,839 | 12/1998 | Gallop et al. | 436/518 |
| 5,876,727 | 3/1999 | Swain et al. | 424/193.1 |
| 5,891,643 | 4/1999 | Fesik et al. | 435/7.1 |

FOREIGN PATENT DOCUMENTS

| | | |
|---|---|---|
| 2240325 | 6/1998 | (CA) . |
| 92/05802 | 4/1992 | (WO) . |
| 93/06121 | 4/1993 | (WO) . |
| 96/40682 | 12/1996 | (WO) . |
| 98/25920 | 6/1998 | (WO) . |

OTHER PUBLICATIONS

Brenner, et al. "Encoded Combinatorial Chemistry." *Proc. Natl. Acad. Sci., USA*. 89:5181 (1992).

McIntosh, et al. "A Nicotinic Acetylcholine Receptor Ligand of Unique Specificity, a Conotoxin ImI." *J. Biol. Chem.* 269(24):16733–16739 (1994).

Myers, et al. "a–Conotoxins, Small Peptide Probes of Nicotinic Acetylcholine Receptors." *Biochemistry*. 30:9370–9377 (1991).

Portoghese, P.S. "The Role of Concepts in Structure–Activity Relationship Studies of Opioid Ligands." *J. Med. Chem.* 35(11): 1927–1937 (1992).

Shuker, et al. "Discovering High–Affinity Ligands For Proteins: SAR by NMR." *Science*. 274:1531–1534 (1996).

Zhang, et al. "Immobilized Nicotinic Receptor Stationary Phase for On–Line Liquid Chromatographic Determination of Drug–Receptor Affinities." *Anal. Biochem.* 264(1): 22–25 (1998).

*Primary Examiner*—Zinna Northington Davis
(74) *Attorney, Agent, or Firm*—Burns, Doane, Swecker & Mathis LLP

(57) ABSTRACT

Novel multibinding compounds are disclosed. The compounds of the invention comprise from 2–10 ligands covalently connected, each of said ligands being capable of binding to an nAChR receptor, thereby modulating the biologcial processes/functions thereof.

10 Claims, 13 Drawing Sheets

FIG. 1
*Starting materials for synthesis of individual ligands*

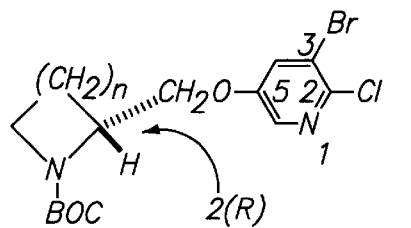

1

Where n=1, preparation is described in Holladay, M.W., et.al., PCT Appl. No. WO 98/25920 (18 June 1998), Example18 (p.58). Prep'n of the 2(S) enantiomer is described in Example 17.

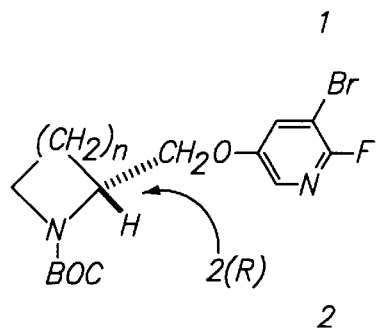

2

Where n=1, preparation is described in Holladay, M.W., et.al., PCT Appl. No. WO 98/25920 (18 June 1998), Example125 (p.115). Prep'n of the 2(S) enantiomer is described in Example 31(p 69).

Where n=2, the procedures used in the preparation where n=1 are used except that 1-BOC-2(R)[or 2(S)] -pyrrolinylmethanol is used in place of 1-BOC-2(R)[or 2(S)] -azetidinemethanol.

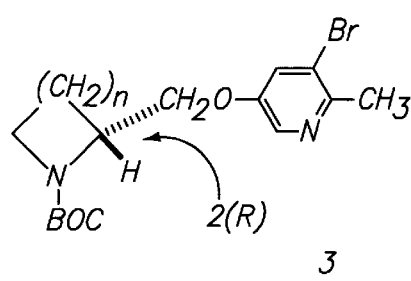

3

Where n=1, preparation is described in Holladay, M.W., et.al., PCT Appl. No. WO 98/25920 (18 June 1998), Example 51 (p.77). Prep'n of the 2(S) enantiomer is described in Example 34 (p 74).

Where n=2, the procedures used in the preparation where n=1 are used except that 1-BOC-2(R)[or 2(S)] -pyrrolinylmethanol is used in place of 1-BOC-2(R)[or 2(S)] -azetidinemethanol.

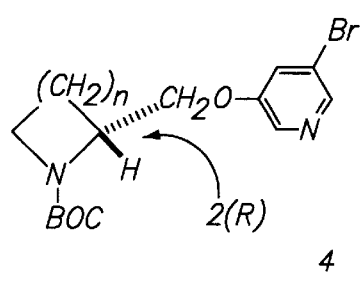

4

Where n=1, preparation is described in Holladay, M.W., et.al., PCT Appl. No. WO 98/25920 (18 June 1998), Example 39 (p.77). Prep'n of the 2(S) enantiomer is described in Example 12 (p 53).

Where n=2, the procedures used in the preparation where n=1 are used except that 1-BOC-2(R)[or 2(S)] -pyrrolinylmethanol is used in place of 1-BOC-2(R)[or 2(S)] -azetidinemethanol.

where B—COOH and BR₂ are as defined in Fig. 13

Example 15

ANALGESIC AGENTS

CROSS REFERENCE TO RELATED APPLICATIONS

This application claims priority under 35 U.S.C. §§119 and/or 120 to U.S. Ser. No. 09/327,044 filed on Jun. 7, 1999 now abandoned; the entire content of which is hereby incorporated by reference, which claims the benefit of U.S. Provisional Application Ser. No. 60/088,466, filed Jun. 8, 1998, and No. 60/092,938, filed Jul. 15, 1998, both of which are incorporated by reference in their entirety.

BACKGROUND OF THE INVENTION

1. Field of the Invention

This invention relates to novel therapeutic compounds that act as analgesics. These agents exert their beneficial effects by binding to nicotinic acetylcholine receptors (nAChRs) and modulating their activity, thus providing a therapeutic effect. More particularly, the invention relates to novel therapeutic compounds that bind to nAChRs and modulate their activity by acting as multibinding agents. The multibinding agents of the invention comprise from 2–10 ligands covalently connected by a linker or linkers, wherein said ligands in their monovalent (i.e. unlinked) state are capable of binding to nAChRs and modulating their activity. The manner in which the ligands are linked is such that the multibinding agents so constructed demonstrate an increased biological and/or therapeutic effect as compared to the same number of unlinked ligands available for binding to nAChRs.

The compounds of the invention are particularly useful in treating pain in mammals. Accordingly, the invention also relates to pharmaceutical compositions comprising a pharmaceutically acceptable excipient and an effective amount of a compound of the invention, and to methods of using such compounds and pharmaceutical compositions containing them for the treatment of such conditions.

Still further, the invention relates to methods of preparing such compounds.

2. State of the Art

The search for compounds that alleviate pain continues to be a major research effort of the pharmaceutical industry. A variety of commercial and experimental drugs having an analgesic effect are known. For example, the opioid drugs, including opium and opium derivatives, have been in use for many years. These drugs, which act as ligands for opioid receptors, inhibit the transmission of sensory stimuli. Unfortunately, treatment with the opioids may result in undesirable side effects, such as constipation, respiratory depression, addiction, and analgesic tolerance.

Another class of analgesics, known as non-steroidal anti-inflammatory drugs (NSAIDS), are also used to relieve pain. These drugs are effective as analgesics because they inhibit the activity of cyclooxygenases, enzymes that regulate the synthesis of proinflainmatory mediators. The pro-inflammatory mediators, such as prostaglandins and other autocoids, are produced at sites of tissue damage and are a cause of pain. Like the opioid drugs, NSAIDS often cause unpleasant side effects, such as gastrointestinal ulceration and bleeding.

Nicotine and its derivative, epibatidine, produce analgesia. Nicotine, however, is only mildly effective as an analgesic (and is extremely toxic), and treatment with this compound often results in physical dependence. Epibatidine, on the other hand, is a potent analgesic, but also produces serious side effects including hypertension, neuromuscular paralysis, and seizures.

Nicotine and epibatidine exert their biological effects in part by binding to nAChR, a family of receptors widespread in the CNS, PNS, and muscle, and modulating their activity. The nAChR are membrane bound homo- or hetero- pentameric proteins consisting of subunits known as $\alpha$, $\beta$, $\gamma$, $\delta$ and $\epsilon$. The subunit composition of the nAChR varies with location. For example, neuronal nAChR, located in the CNS, exists in two forms: 1) homopentameric proteins, consisting of the $\alpha_7$ subunits; and 2) heteropentameric proteins, consisting of $\alpha_4\beta_2$ subunits. The nAChRs located at the neuromuscular junction and at the sympathetic ganglia consist of $\alpha_1 B_1 \delta \gamma(\epsilon)$ and $\alpha_3$, respectively.

Nicotine and epibatidine are ligands that bind nonspecifically to all nAChR. However, the binding of ligands to the neuromuscular type of nAChR does not produce an analgesic effect. In fact this nonspecific binding may result in the detrimental side effects of these drugs. A useful strategy for drug design, therefore, is to synthesize ligands that bind with high specificity to the type of nAChR involved in the perception of pain, such as the neuronal nAChR.

Recently clinically useful variants of epibatidine have been developed (WO 9825920) that result in fewer unpleasant sequela in treated individuals. However, the clinical shortcomings of these drugs and other drugs in current usage are considerable. There continues to exist a need for novel compounds that provide broad spectrum pain relief, including pain due to acute or persistent injury such as that generated from neuropathological processes. Improvements on existing drugs could include greater tissue selectivity, increased efficacy, reduced side effects and a more favorable duration of action.

The multibinding compounds of the present invention fulfill this need.

SUMMARY OF THE INVENTION

This invention relates to novel multibinding compounds that act as analgesics by binding to nicotinic acetylcholine receptors (nAChRs) and modulating their activity.

Accordingly, in one aspect, the present invention relates to novel multibinding agents wherein a multibinding agent comprises 2–10 ligands, which may be the same or different, covalently connected by a linker or linkers, which may be the same or different, each of said ligands comprising a ligand domain capable of binding to an nAChR.

The preferred multibinding agents are represented by Formula I:

    I in which
- L is a ligand that may be the same or different at each occurrence;
- X is a linker that may be the same or different at each occurrence;
- p is an integer of 2–10; and
- q is an integer of 1–20; or
- a pharmaceutically acceptable salt or prodrug thereof;

wherein each of said ligands comprising a ligand domain state capable of binding to an nAChR.

Preferably, q is less than p. More preferably, each ligand L is a compound of formula (a):

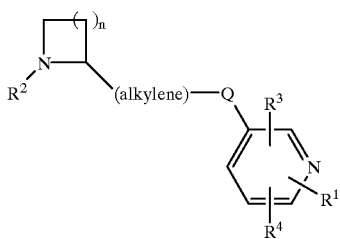

(a)

wherein:

n is an integer of 1–3;

$R^2$ is hydrogen, alkyl, or a covalent bond connecting the ligand to a linker;

Q is —O—, —$NR^5$— (where $R^5$ is hydrogen, alkyl, a prodrug derivative, or a covalent bond connecting the ligand to a linker), or —S(O)$n^1$ (where $n^1$ is 0 to 2);

$R^1$ is hydrogen, halo, cyano, haloalkyl, alkoxy, alkyl, or a covalent bond connecting the ligand to a linker;

$R^3$ is hydrogen, halo, or a covalent bond connecting the ligand to a linker; and $R^4$ is hydrogen, halo, alkyl, alkenyl, alkynyl, nitro, alkoxy, or a covalent bond connecting the ligand to a linker;

or a pharmaceutically acceptable salt thereof;

provided that at least one of $R^1$, $R^2$, $R^3$, and $R^4$ is a covalent bond connecting the ligand to a linker.

Still more preferably, each linker X in the multibinding compound of Formula I independently has the formula:

$$-X^a-Z^a-(Y^a-Z^a)_m-X^a-$$

wherein:

m is an integer of from 0 to 20;

$X^a$ at each separate occurrence is selected from the group consisting of —O—, —S—, —NR—, —C(O)—, —C(O)O—, —OC(O)—, —C(O)NR—, —NRC(O)—, C(S), —C(S)O—, —C(S)NR—, —NRC(S)—, or a covalent bond where R is as defined below;

$Z^a$ at each separate occurrence is selected from the group consisting of alkylene, substituted alkylene, cycloalkylene, substituted cylcoalkylene, alkenylene, substituted alkenylene, alkynylene, substituted alkynylene, cycloalkenylene, substituted cycloalkenylene, arylene, heteroarylene, heterocyclene, or a covalent bond;

each $Y^a$ at each separate occurrence is selected from the group consisting of —O—, —C(O)—, —OC(O)—, —C(O)O—, —NR—, —S(O)n—, —C(O)NR'—, —NR'C(O)—, —NR'C(O)NR'—, —NR'C(S)NR'—, —C(=NR')—NR'—, —NR'—C(=NR')—, —OC(O)—NR'—, —NR'—C(O)—O—, —N=C($X^a$)—NR'—, —NR'—C($X^a$)=N—, —P(O)(OR')—O—, —P(O)(OR')—, —S(O)$_n$CR'R"—, —S(O)$_n$—NR'—, —NR'—S(O)$_n$—, —S—S—, and a covalent bond; where n is 0, 1 or 2; and R, R' and R" at each separate occurrence are selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic.

In a second aspect, the invention relates to a method of providing analgesia in a mammal, comprising administering to a subject in need of such treatment a therapeutically effective amount of a multibinding agent of Formula I.

In a third aspect, the invention relates to a pharmaceutical composition comprising a therapeutically effective amount of one or more multibinding agents, or a pharmaceutically acceptable salt thereof, said multibinding agent comprising 2–10 ligands, which may be the same or different, covalently connected by a linker or linkers, which may be the same or different, each of said ligands compromising a ligand domain capable of binding to an nAChR receptor, admixed with at least one pharmaceutically acceptable excipient.

In a fourth aspect, the invention relates to a pharmaceutical composition comprising a therapeutically effective amount of one or more compounds of Formula I, or a pharmaceutically available salt thereof, admixed with at least one pharmaceutically acceptable excipient.

In a fifth aspect, the invention relates to processes for preparing the compounds of the invention, in particular the compounds of Formula I.

In a sixth aspect, the invention relates to a method for identifying a multibinding agent capable of binding to an nAChR receptor, comprising preparing an array of multimeric agents, contacting the multimeric agent array with an nAChR receptor, and selecting a multibinding agent based upon its ability to bind to the nAChR receptor.

BRIEF DESCRIPTION OF THE DRAWINGS

FIGS. 1–12 and the accompanying table illustrate various aspects of the invention.

DETAILED DESCRIPTION OF THE INVENTION

Figure 2:
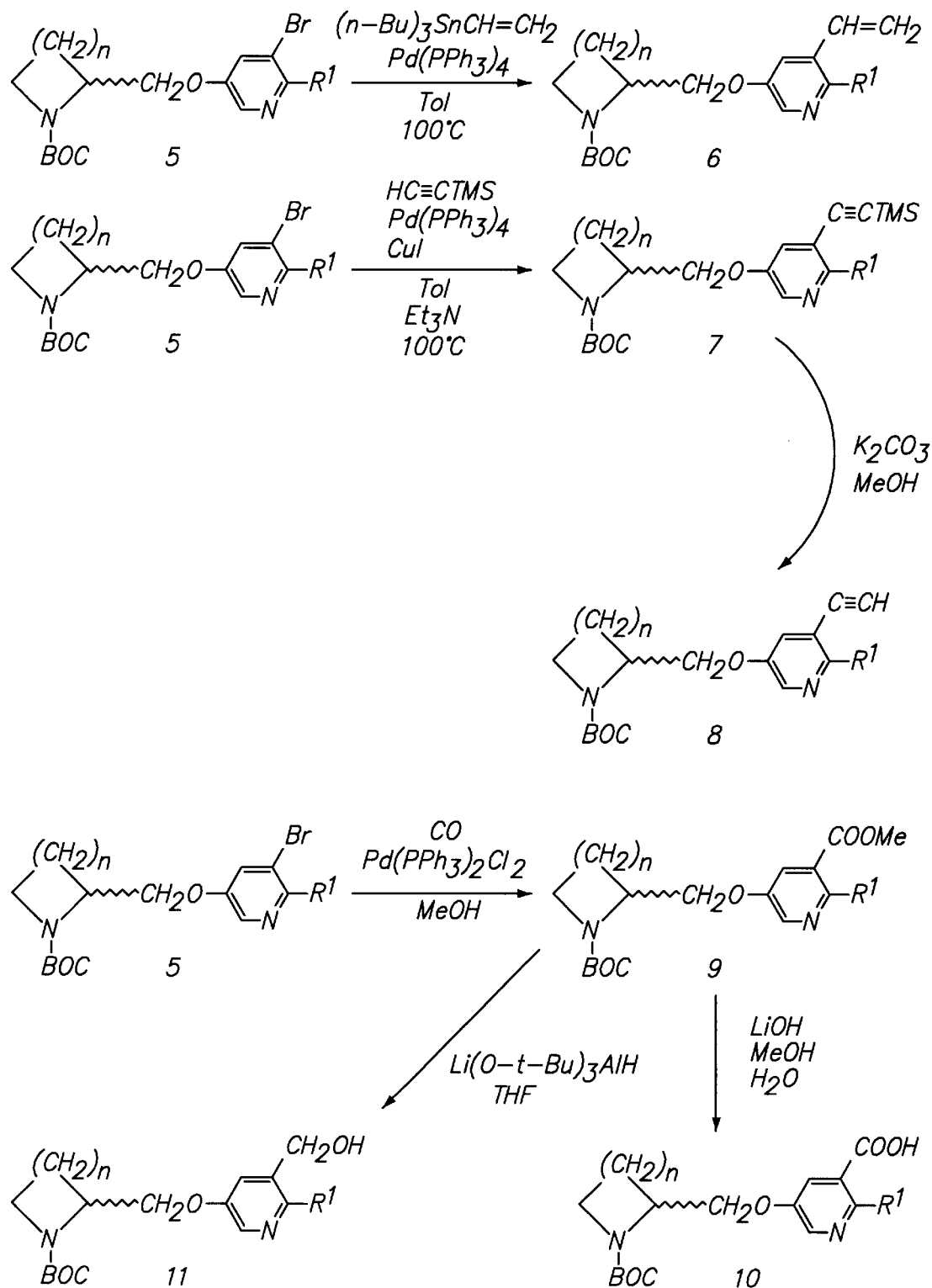

Biological systems in general involve molecular interactions between bioactive ligands and their receptors, in which the receptor "recognizes" a molecule (a ligand) or portion of a molecule (a ligand domain). One example of this process is the interaction between ligands (drugs) and nAChR. The result of this interaction can be either to initiate the desired biological effect of the nAChR receptor, or alternatively to inhibit or alter (i.e. to modulate) the normal function of the nAChR receptor. Accordingly, the modulation of such processes is regarded as an important target for drug development.

The interaction of an nAChR receptor with a ligand may be described in terms of "affinity" and "specificity". The affinity and specificity of any given ligand/receptor interaction are dependent upon the complementarily of molecular binding surfaces and the energetic costs of complexation. Affinity may be quantified by the equilibrium constant of complex formation. Specificity relates to the difference in affinity between different ligands binding to the same receptor subtype, or the same ligand binding to different receptor subtypes.

The compounds of the invention are multibinding agents, and although not wishing to be bound or restricted by any particular theory or proposed mechanism of action, it is believed that the surprising activity of these compounds at least in part arises from their ability to bind in a multivalent manner with nAChR (i.e. the ligand binding site), and thus lowering the energetic costs of binding. Multivalent binding interactions are characterized by the concurrent interaction of at least two ligands of a multibinding agent with multiple ligand binding sites, which may be present on multiply distinct nAChR receptors or present as multiple distinct binding sites on a single nAChR receptor. Multivalent interactions differ from collections of individual monovalent interactions by the phenomenon of energetic coupling, wherein the binding of one ligand of a multibinding agent to its receptor will typically affect the thermodynamics of binding of a second ligand of the same multibinding agent thus giving rise to an enhanced biological effect.

DEFINITIONS

When discussing the compounds, compositions or methods of the present invention, the following terms have the following meanings unless otherwise indicated. Any undefined terms have their art recognized meanings.

The term "alkyl" refers to a monoradical branched or unbranched saturated hydrocarbon chain, preferably having from 1 to 40 carbon atoms, preferably 1–10 carbon atoms, more preferably 1–6 carbon atoms, such as methyl, ethyl, n-propyl, isopropyl, n-butyl, secondary butyl, tert-butyl, n-hexyl, n-octyl, n-decyl, n-dodecyl, 2-ethyldodecyl, tetradecyl, and the like, unless otherwise indicated.

The term "substituted alkyl" refers to an alkyl group as defined above having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "alkylene" refers to a diradical of a branched or unbranched saturated hydrocarbon chain, preferably having from 1 to 40 carbon atoms, preferably 1–10 carbon atoms, more preferably 1–6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to:

(a) an alkylene group as defined above having from 1 to 5 substituents selected from the group consisting of alkoxy, substituted alkoxy, cycloalkyl, substituted cycloalkyl, cycloalkenyl, substituted cycloalkenyl, acyl, acylamino (including, for example, N-glucosaminecarbonyl, benzoylamino, biphenylcarbonylamino, and the like), acyloxy, amino, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocyclooxy, nitro, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group.

(b) an alkylene group as defined above that is interrupted by 1–20 atoms or substituents independently chosen from oxygen, sulfur and NR$^a$—, wherein R$^a$ is chosen from hydrogen, alkyl, substituted alkyl, cycloalkyl, alkenyl, cycloalkenyl, alkynyl, aryl, heteroaryl and heterocyclic; or (c) an alkylene group as defined above that has both from 1 to 5 substituents as defined above and is also interrupted by 1–20 atoms as defined above.

Examples of substituted alkylenes are chloromethylene (—CH(Cl)—), aminoethylene (—CH(NH$_2$)CH$_2$—), 1-(dodecanoylamino)propylene (—CH[NHC(O)—(CH$_2$)$_{11}$—CH$_3$]CH$_2$—), 1-(4-phenylbenzoylamino)pentylene (—CH[NHC(O)—Z](CH$_2$)$_4$), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—CH$_2$O—CH$_2$CH$_2$—), and the like.

The term "alkaryl" or "aralkyl" refers to the groups -alkylene-aryl and -substituted alkylene-aryl in which alkylene and aryl are as defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Examples of such groups are methylenemethoxy (—CH$_2$—OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

The term "alkenyl" refers to a monoradical of a branched or unbranched unsaturated hydrocarbon preferably having from 2 to 40 carbon atoms, preferably 2–10 carbon atoms, more preferably 2–6 carbon atoms, and preferably having 1–6 double bonds. This term is further exemplified by such radicals as vinyl, prop-2-enyl, pent-3-enyl, hex-5-enyl, 5-ethyldodec-3,6-dienyl, and the like.

The term "substituted alkenyl" refers to an alkenyl group as defined above having from 1 to 5 substituents selected from the group consisting of alkoxy, substituted alkoxy, acyl, acylamino, acyloxy, amino, aminoacyl, aminoacyloxy, oxyaminoacyl, azido, cyano, halogen, hydroxyl, keto, thioketo, carboxyl, carboxylalkyl, thiol, thioalkoxy, substituted thioalkoxy, aryl, heteroaryl, heterocyclic, aryloxy, thioaryloxy, heteroaryloxy, thioheteroaryloxy, heterocyclooxy, thioheterocyclooxy, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and. —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "alkenylene" refers to a diradical of an unsaturated hydrocarbon, preferably having from 2 to 40 carbon atoms, preferably 2–10 carbon atoms, more preferably 2–6 carbon atoms, and preferably having 1–6 double bonds. This term is further exemplified by such radicals as 1,2-ethenyl, 1,3-prop-2-enyl, 1,5-pent-3-enyl, 1,4-hex-5-enyl, 5-ethyl-1, 12-dodec-3,6-dienyl, and the like.

The term "substituted alkenylene" refers to an alkenylene group as defined above having from 1 to 5 substituents, selected from the group consisting of alkoxy, substituted alkoxy, acyl, acylamino, acyloxy, amino, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocyclooxy, nitro, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monoradical of an unsaturated hydrocarbon, preferably having from 2 to 40 carbon atoms, preferably 2–10 carbon atoms, more preferably 2–6 carbon atoms, and preferably having 1–6 triple bonds. This term is further exemplified by such radicals as acetylenyl, prop-2-ynyl, pent-3-ynyl, hex-5-ynyl, 5-ethyldodec-3,6-diynyl, and the like.

The term "substituted alkynyl" refers to an alkynyl group as defined above having from 1 to 5 substituents, selected from the group consisting of alkoxy, substituted alkoxy, acyl, acylamino, acyloxy, amino, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocycloxy, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, SO$_2$-heterocyclic, NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "alkynylene" refers to a diradical of an unsaturated hydrocarbon radical, preferably having from 2 to 40 carbon atoms, preferably 2–10 carbon atoms, more preferably 2–6 carbon atoms, and preferably having 1–6 triple bonds. This term is further exemplified by such radicals as 1,3-prop-2-ynyl, 1,5-pent-3-ynyl, 1,4-hex-5-ynyl, 5-ethyl-1, 12-dodec-3,6-diynl, and the like.

The term "acyl" refers to the groups —CHO, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl).

Unless otherwise constrained by the definition for the aryl substituent, such aryl groups can optionally be substituted with from 1 to 5 substituents selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$— substituted alkyl, —SO$_2$-aryl, —SO$_2$-heteroaryl, trihalomethyl, NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to a diradical derived from aryl or substituted aryl as defined above, and is exemplified by 1,2-phenylene, 1,3-phenylene, 1,4-phenylene, 1,2-naphthylene and the like.

The term "carboxyalkyl" refers to the group "—C(O)Oalkyl" where alkyl is as defined above.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents selected from the group consisting of alkoxy, substituted alkoxy, cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "cycloalkenyl" refers to cyclic alkenyl groups of from 4 to 20 carbon atoms having a single cyclic ring or fused rings and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "halo" or "halogen" refers to fluoro, chloro, bromo and iodo.

The term "haloalkyl" refers to alkyl as defined above substituted by 1–4 halo groups as defined above, which may be the same or different, such as 3-fluorododecyl, 12,12,12-trifuorododecyl, 2-bromooctyl, -3-bromo-6-chloroheptyl, and the like.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO2-aryl, —SO$_2$-heteroaryl, trihalomethyl, mono-and di-alkylamino, mono- and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Preferred heteroaryls include pyridyl, pyrrolyl and furyl.

The term "heteroaryloxy" refers to the group heteroaryl-O—.

The term "heteroarylene" refers to the diradical group derived from heteroaryl or substituted heteroaryl as defined above, and is exemplified by the groups 2,6-pyridylene, 2,4-pyridiylene, 1,2-quinolinylene, 1,8-quinolinylene, 1,4-benzofuranylene, 2,5-pyridinylene, 1,3-morpholinylene, 2,5-indolenyl, and the like.

The term "heterocycle" or "heterocyclic" refers to a monoradical saturated or unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Such heterocyclic groups can have a single ring or multiple condensed rings.

Examples of heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

One class of heterocyclics include "crown compounds" which refers to a specific class of heterocyclic compounds having one or more repeating units of the formula [—(CH$_2$—)$_m$Y—] where m is equal to or greater than 2, and Y at each separate occurrence can be O, N, S or P. Examples of crown compounds include, by way of example only, [—(CH$_2$)$_3$—NH—]$_3$, [—((CH$_2$)$_2$—O)$_4$—((CH$_2$)$_2$—NH)$_2$] and the like. Typically such crown compounds can have from 4 to 10 heteroatoms and 8 to 40 carbon atoms.

The term "heterocyclooxy" refers to the group heterocyclic-O—.

The term "thioheterocyclooxy" refers to the group heterocyclic-S—.

The term "heterocyclene" refers to the diradical group derived from a heterocycle as defined herein, and is exemplified by the groups 2,6-morpholino, 2,5-morpholino and the like.

The term "oxyacylamino" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

The term "alkyl optionally interrupted by 1–5 atoms chosen from O, S, or N" refers to alkyl as defined above in which the carbon chain is interrupted by O, S, or N. Within the scope are ethers, sulfides, and amines, for example 1-methoxydecyl, 1-pentyloxynonane, 1-(2-isopropoxyethoxy)-4-methylnonane, 1-(2-ethoxyethoxy)dodecyl, 2-(t-butoxy)heptyl, 1-pentylsulfanylnonane, nonylpentylamine, and the like.

"Heteroarylalkyl" refers to heteroaryl as defined above linked to alkyl as defined above, for example pyrid-2-ylmethyl, 8-quinolinylpropyl, and the like.

"Optional" or "optionally" means that the subsequently described event or circumstance may or may not occur, and that the description includes instances where said event or circumstance occurs and instances in which it does not. For example, optionally substituted alkyl means that alkyl may or may not be substituted by those groups enumerated in the definition of substituted alkyl.

"Ligand" as used herein denotes a compound that is a binding partner for an nAChR receptor and is bound thereto by complementarity. The specific region or regions of the ligand that is (are) recognized by the nAChR receptor is designated as the "ligand domain". By virtue of the ligand domain, a ligand may be either capable of binding to an nAChR receptor by itself, or may require the presence of one or more non-ligand components for binding (e.g. $Ca^{2+}$, $Mg^{2+}$, or a water molecule is required for the binding of a ligand domain to various receptors).

Examples of ligands useful in this invention, include 3-pyridyloxy alkylene azetidin-2-yl compounds and derivatives of 3-pyridyloxy alkylene azetidin-2yl, as described below. Those skilled in the art will appreciate that portions of the ligand structure that are not essential for molecular recognition and binding activity (i.e. that are not part of the ligand domain) may be varied substantially, replaced or substituted with unrelated structures (for example, with ancillary groups as defined below), and, in some cases, omitted entirely without affecting the binding interaction. Accordingly, it should be understood that the term ligands is not intended to be limited to compounds known to be useful as nAChR agonists, modulators, or the like. (for example, known drugs). Those skilled in the art will understand that the term ligand can equally apply to a molecule that is not normally recognized as having useful properties related to binding to an nAChR receptor, in that ligands that exhibit minimally useful properties as monomers can be highly active as multibinding agents, due to the biological benefit (increased biological effect) conferred by multivalency. The primary requirement for a ligand as defined herein is that it has a ligand domain as defined above.

The preferred ligands include 3-pyridyloxy alkylene azetidin-2-yl and its derivatives. It should be understood that the term "ligand" or "ligands" is intended to include enantiomers of 3-pyridyloxy alkylene azetidin-2-yl, that is both (R) and (S) compounds and stereoisomers of the ligands, including pure enantiomers and non-racemic mixtures thereof. The scope of the invention, as described and claimed, encompasses the racemic forms of the ligands as well as the individual enantiomers and non-racemic mixtures thereof.

"Multibinding agent" or "multibinding compound" as used herein refers to a compound that is capable of multivalency as defined herein, and which has 2–10 ligands as defined herein, which may be the same or different, connected by one or more covalent linker or linkers, which may be the same or different, preferably from 1–20 in number. A multibinding agent provides an improved biological and/or therapeutic effect as measured against that achieved by the same number of unlinked ligands available for binding to the ligand binding site of the nAChR receptor. Examples of increased biological and/or therapeutic effect with respect to the target include, for example, increased specificity, increased affinity, increased selectivity, increased potency, increased efficacy, increased therapeutic index, a change in the duration of action, decreased toxicity, decreased side effects, improved bioavailability, improved pharmacokinetics, improved activity spectrum, and the like. The multibinding compounds of the invention exhibit one or more of the foregoing effects.

"Potency" as used herein refers to the minimum concentration at which a ligand is able to achieve a desirable biological or therapeutic effect. The potency of a ligand is typically proportional to its affinity for its ligand binding site. In some cases, the potency may be non-linearly correlated with its affinity. In comparing the potency of two drugs, e.g., a multibinding agent and the aggregate of its unlinked ligand, the dose-response curve of each is determined under identical test conditions (e.g., in an in vitro or in vivo assay or in an appropriate animal model, such as a human patient. The finding that the multibinding agent produces an equivalent biological or therapeutic effect at a lower concentration than the aggregate unlinked ligand (e.g., on a per weight, per mole, or per ligand basis) is indicative of enhanced potency.

"Univalency" as used herein refers to a single binding interaction between the ligand domain of one ligand as defined herein with the ligand recognition site of an nAChR receptor. It should be noted that a compound having multiple copies of a ligand (or ligands) exhibits univalency when only one ligand of that compound is interacting with a ligand binding site. Examples of univalent interactions are depicted below where the arrow represents a ligand domain and the indent represents the ligand binding site of a receptor.

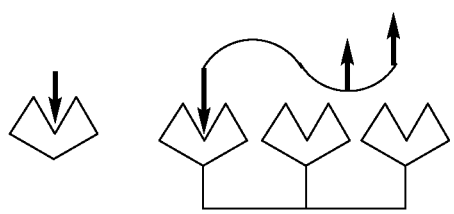

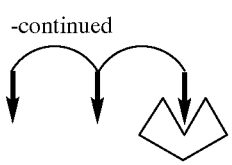

"Multivalency" as used herein refers to the concurrent binding of 2 to 10 linked ligands (which may be the same or different) and two or more corresponding ligand binding sites of one or more nAChR.

Accordingly, two ligands connected by a linker that bind concurrently to two ligand binding sites of one or more nAChR would be considered to be a bivalent compound; similarly, three ligands thus connected provide a trivalent compound. An example of trivalent binding, illustrating a multibinding agent bearing three ligands is shown below.

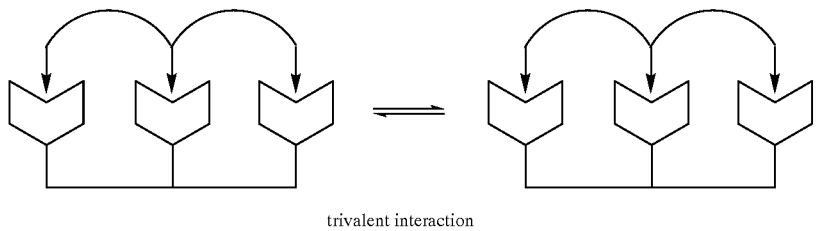

trivalent interaction

It should be understood that all compounds that contain multiple copies of a ligand attached to a linker (or linkers) do not necessarily exhibit the phenomena of multivalency, i.e. that improved biological and/or therapeutic effect of the multibinding agent is obtained as measured against that produced by the same number of unlinked ligands available for binding to a ligand binding site. For multivalency to occur, the ligand domains of the ligands that are connected by a linker have to be presented to their appropriate receptor (s) (i.e. the ligand binding sites) by the linker in a specific manner in order to bring about the desired ligand-orienting result, and thus produce a multibinding event. Thus, the term "multimeric ligand compound" refers to multiple copies of a ligand attached to a linker (or linkers) that may or may not exhibit the phenomena of multivalency. "Multimeric ligand compound library" refers to the collection of multimeric ligand compounds that are provided by the synthetic methods disclosed herein.

"Selectivity" or "specificity" is a measure of the binding preferences of a ligand for different receptors and/or different ligands for the same receptor. The selectivity of a ligand with respect to its target receptor relative to another receptor is given by the ratio of the respective values of $K_d$ (i.e., the dissociation constants for each ligand-receptor complex), or in cases where a biological effect is observed below the $K_d$, selectivity is given by the ratio of the respective $EC_{50}$s (i.e. the concentrations that produce 50% of the maximum response for the ligand interacting with the two distinct receptors).

The term "ligand recognition site" or "ligand binding site" as used herein denotes the site on an nAChR receptor that recognizes a ligand domain and provides a binding partner for a ligand. The ligand binding site may be defined by monomeric or multimeric structures. This interaction may be capable of producing a unique biological effect, for example, agonism, antagonism, modulatory effect, and the like, or may maintain an ongoing biological effect.

It should be recognized that the ligand binding sites of receptors that participate in biological multivalent binding interactions are constrained to varying degrees by their intra- and intermolecular associations (e.g., they may be covalently joined in a single or multiple structure, noncovalently associated in a multimeric structure, embedded in a membrane or polymeric matrix, and so on) and therefore have less relative translational and rotational freedom than if the same receptors were present as monomers in solution.

The terms "agonism" and "antagonism" are well known in the art. By the term "modulatory effect" we mean the ability of a ligand to change the biological effect of an agonist or antagonist through binding to a receptor.

As used herein, the terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$), diethyl ether, ethyl acetate, acetone, methylethyl ketone, methanol, ethanol, propanol, isopropanol, tert-butanol, dioxane, pyridine, and the like]. Unless specified to the contrary, the solvents used in the reactions of the present invention are inert solvents.

"Pharmaceutically acceptable salt" means those salts which retain the biological effectiveness and properties of the multivalent compounds of the invention, and which are not biologically or otherwise undesirable. The multivalent compounds of the invention are capable of forming both acid and base salts by virtue of the presence of amino and carboxyl groups respectively.

1. Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylarnine, trimethyl amine, diethylamine, triethylamine, tripropylamine, ethanolamine, 2-dimmethylaminoethanol, tromethamine, lysine, arginine, histidine, caffeine, procaine, hydrabarnine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl)carboxamides, and the like.

2. Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "treatment" as used herein covers any treatment of a condition or disease in an animal, particularly a mammal, more particularly a human, and includes:

(i) preventing the disease or condition from occurring in a subject which may be predisposed to the disease but has not yet been diagnosed as having it;

(ii) inhibiting the disease or condition, i.e. arresting its development;

(iii) relieving the disease or condition, i.e. causing regression of the condition; or (iv) relieving the conditions caused by the disease, i.e. symptoms of the disease.

The term "disease or condition which is alleviated by treatment with a multibinding agent" as used herein covers all conditions and disease states which are generally acknowledged in the art to be usefully treated with the ligands as defined in general, and those disease states which have been found to be usefully treated by the specific multibinding agents of our invention, including the compounds of Formula I. The term covers prophylactic treatment as well as relief or regression of the disease. It also covers the treatment of conditions that are not necessarily considered as disease states, for example the use of multibinding agents as contraceptives, as pregnancy limiting agents, for the treatment of insomnia, treatment of obesity, and the like.

Such disease states include, but are not limited to, treatment of a mammal for modifying physiological functions related to movement or cognition or pathological sequela, such as pain and the like.

The term "therapeutically effective amount" refers to that amount of a multibinding agent, for example a compound of Formula I, that is sufficient to effect treatment, as defined above, when administered to a mammal or avian in need of such treatment. The therapeutically effective amount will vary depending on the subject and disease state being treated, the severity of the affliction and the manner of administration, and the like, and may be determined routinely by one of ordinary skill in the art.

The term "protecting group" or "blocking group" refers to any group which when bound to one or more hydroxyl, thiol, amino or carboxyl groups of the compounds prevents reactions from occurring at these groups and which protecting group can be removed by conventional chemical or enzymatic steps to reestablish the hydroxyl, thio, amino or carboxyl group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product. Protecting groups are disclosed in more detail in T. W. Greene and P. G. M. Wuts, "Protective Groups in Organic Synthesis" $2_{nd}$ Ed., 1991, John Wiley and Sons, New York.

Preferred removable amino blocking groups include conventional substituents such as t-butyloxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product.

Preferred carboxyl protecting groups include esters such as methyl, ethyl, propyl, t-butyl etc. which can be removed by mild conditions compatible with the nature of the product.

"Linker" or "linkers" as used herein, identified where appropriate by the symbol X, refers to a group or groups that covalently link(s) from 2–10 ligands (as defined herein) in a manner that provides a compound capable of multivalency. The linker is a ligand domain orienting entity that permits attachment of multiple copies of ligands (which may be the same or different) thereto. The extent to which multivalent binding is realized depends upon the efficiency with which the linker that joins the ligands permits the ligand domains to be presented to the ligand recognition sites substrates). Beyond presenting ligand domains for multivalent interactions with receptors, the linker spatially constrains these interactions to occur within dimensions defined by the linker. Thus, the structural features of the linker (valency, geometry, orienting capabilities, size, flexibility, chemical composition) are features of multibinding agents that play an important role in determining their activities. The term linker, however, does not include solid inert supports such as beads, resins, glass particles, rods, fibers, and the like, but it should be understood that the multibinding compounds of the invention can be attached to a solid support if desired to provide, for example, a material useful for separation and purification processes (e.g. affinity chromatography).

The ligands are covalently attached to the linker or linkers using conventional chemical techniques, for example reaction between a carboxylic acid and an amine to form an amide, an amine and a sulfonyl halide to form a sulfonamide, an alcohol or phenol with an alkyl or aryl halide to form an ether, and the like.

The linker (or linkers) is attached to the ligand at a position such that the ligand domain is permitted to orient itself appropriately in order to bind to the ligand binding site. The term linker embraces everything that is not considered to be part of the ligand.

The relative orientation in which the ligand domains are displayed derives from the particular point or points of attachment of the ligands to the linker, and on the framework geometry. The determination of where acceptable substitutions can be made on a ligand is typically based on prior knowledge of structure-activity relationships of the ligand and/or congeners and/or structural information about ligand-receptor complexes (e.g., from X-ray crystallography, NMR. Such positions and the synthetic methods for covalent attachment are well known in the art.

Suitable linkers are discussed below.

At present, it is preferred that the multibinding agent is a bivalent compound, in which two ligands are covalently linked.

"Biological effect" as used herein includes, but is not limited to, increased affinity, increased selectivity, increased potency, increased efficacy, increased duration of action, decreased toxicity, and the like.

PREFERRED EMBODIMENTS

While the broadest definition of this Invention is set forth in the Summary of the Invention, certain compounds of Formula I are preferred.

A preferred group of compounds is a bivalent multibinding compound of Formula II:

II

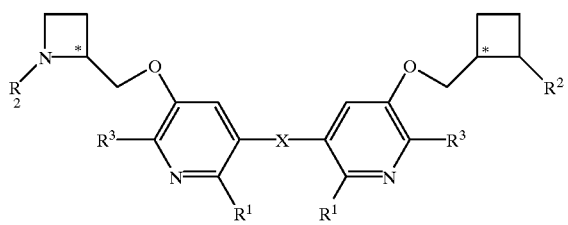

wherein:
- $R^1$ is hydrogen, fluoro, bromo, chloro, cyano, —$CHF_2$, —$OMe$, —$CH_2F$, or $C_{1-2}$-alkyl, preferably hydrogen, methyl, chloro, or bromo;
- $R^2$ is hydrogen or alkyl, preferably hydrogen or methyl, more preferably hydrogen;
- $R^3$ is hydrogen, fluoro, or chloro, preferably hydrogen;
- the stereochemistry at *C is R; and
- X is a linker

GENERAL SYNTHETIC SCHEME

Compounds of this invention can be made by the methods depicted in the reaction schemes shown below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1–15 (John Wiley and Sons, 1991); Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4th Edition), and Larock's Comprehensive Organic Transformations (VCH Publishers Inc., 1989).

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Furthermore, it will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis*, Second Edition, Wiley, New York, 1991, and references cited therein.

These schemes are merely illustrative of some methods by which the compounds of this invention can be synthesized, and various modifications to these schemes can be made and will be suggested to one skilled in the art having referred to this disclosure.

Preparation of a Multibinding Compound of Formula I

In general, a bivalent multibinding compound of Formula I can be prepared as illustrated and described in Schemes A below.

A bivalent multibinding compound of Formula (I) can be prepared by covalently attaching the ligands, L, wherein at least one of the ligand is selected from a compound of formula (a) as defined in the Summary of the Invention, to a linker, X, as shown in Scheme A below.

Scheme A

Method (a)

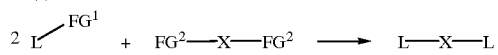

Method (b)

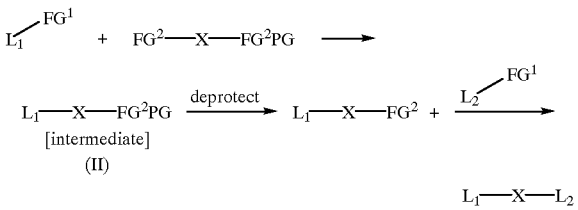

In method (a), a bivalent multibinding compound of Formula (I) is prepared in one step, by covalently attaching the ligands, L, to a linker, X, where $FG^1$ and $FG^2$ represent a functional group such as halo, amino, hydroxy, thio, aldehyde, ketone, carboxy, carboxy derivatives such as acid halide, ester, amido, and the like. This method is preferred for preparing compounds of Formula (I) where the ligands are the same.

In method (b), the compounds of Formula (I) are prepared in a stepwise manner by covalently attaching one equivalent of a ligand, $L_1$, with a ligand X where $FG^1$ and $FG^2$ represent a functional group as defined above, and $FG^2PG$ is a protected functional group to give an intermediate of formula (II). Deprotection of the second functional group on the ligand, followed by reaction with a ligand $L_2$, which may be same or different than ligand $L_1$, then provides a compound of Formula (I). This method is suitable for preparing compounds of Formula (I) where the ligands are the non-identical.

The ligands are covalently attached to the linker using conventional chemical techniques providing for covalent linkage of the ligand to the linker. Reaction chemistries resulting in such linkages are well known in the art and involve the use of complementary functional groups on the linker and ligand as shown in Table I below.

TABLE I

Representative Complementary Binding Chemistries

| First Reactive Group | Second Reactive Group | Linkage |
| --- | --- | --- |
| carboxyl | amine | amide |
| sulfonyl halide | amine | sulfonamide |
| hydroxyl | alkyl/aryl halide | ether |
| hydroxyl | isocyanate | urethane |

TABLE I-continued

Representative Complementary Binding Chemistries

| First Reactive Group | Second Reactive Group | Linkage |
|---|---|---|
| amine | epoxide | β-hydroxyamine |
| amine | alkyl/aryl halide | alkylamine |
| hydroxyl | carboxyl | ester |
| amine | isocyanate | urea |

Reaction between a carboxylic acid of either the linker or the ligand and a primary or secondary amine of the ligand or the linker in the presence of suitable, well-known activating agents such as dicyclohexylcarbodiimide, results in formation of an amide bond covalently linking the ligand to the linker; reaction between an amine group of either the linker or the ligand and a sulfonyl halide of the ligand or the linker, in the presence of a base such as triethylamine, pyridine, an the like results in formation of a sulfonamide bond covalently linking the ligand to the linker; and reaction between an alcohol or phenol group of either the linker or the ligand and an alkyl or aryl halide of the ligand or the linker in the presence of a base such as triethylamine, pyridine, and the like, results in formation of an ether bond covalently linking the ligand to the linker.

Compounds of formula (a) can be prepared by the procedures described in PCT Application Publication No. WO 98/25920 which is herein incorporated by reference in its entirety.

Detailed descriptions of the synthesis of compounds of Formula I are provided in Examples 1–15 below.

Any compound which binds to an nAChR can be used as a ligand in this invention. Typically, a compound selected for use as a ligand will have at least one functional group, such as an amino, hydroxyl, thiol or carboxyl group and the like, which allows the compound to be readily coupled to the linker. Compounds having such functionality are either known in the art or can be prepared by routine modification of known compounds using conventional reagents and procedures.

Linkers can be attached to different positions on the ligand molecule to achieve different orientations of the ligand domains, and thereby facilitate multivalency. While a number of positions on ligands are synthetically practical for linking, it is preferred to preserve those ligand substructures which are most important for ligand-receptor binding. At present, the pyridyl group and the nitrogen atom of the azetidine ring are preferred points of attachment.

It will be apparent to one skilled in the art that the above chemistries are not limited to preparing bivalent multibinding compounds of Formula (I) and can be used to prepare tri-, tetra-, etc., multibinding compounds of Formula (I).

The linker is attached to the ligand at a position that retains ligand domain-ligand binding site interaction and specifically which permits the ligand domain of the ligand to orient itself to bind to the ligand binding site. Such positions and synthetic protocols for linkage are well known in the art. The term linker embraces everything that is not considered to be part of the ligand.

The relative orientation in which the ligand domains are displayed derives from the particular point or points of attachment of the ligands to the linker, and on the framework geometry. The determination of where acceptable substitutions can be made on a ligand is typically based on prior knowledge of structure-activity relationships (SAR) of the ligand and/or congeners and/or structural information about ligand-receptor complexes (e.g., X-ray crystallography, NMR, and the like). Such positions and the synthetic methods for covalent attachment are well known in the art. Following attachment to the selected linker (or attachment to a significant portion of the linker, for example 2–10 atoms of the linker), the univalent linker-ligand conjugate may be tested for retention of activity in the relevant assay.

The linker, when covalently attached to multiple copies of the ligands, provides a biocompatible, substantially non-immunogenic multibinding compound. The biological activity of the multibinding compound is highly sensitive to the valency, geometry, composition, size, flexibility or rigidity, etc. of the linker and, in turn, on the overall structure of the multibinding compound, as well as the presence or absence of anionic or cationic charge, the relative hydrophobicity/hydrophilicity of the linker, and the like on the linker. Accordingly, the linker is preferably chosen to maximize the biological activity of the multibinding compound. The linker may be chosen to enhance the biological activity of the molecule. In general, the linker may be chosen from any organic molecule construct that orients two or more ligands to their ligand binding sites to permit multivalency. In this regard, the linker can be considered as a "framework" on which the ligands are arranged in order to bring about the desired ligand-orienting result, and thus produce a multibinding compound.

For example, different orientations can be achieved by including in the framework groups containing mono- or polycyclic groups, including aryl and/or heteroaryl groups, or structures incorporating one or more carbon-carbon multiple bonds (alkenyl, alkenylene, alkynyl or alkynylene groups). Other groups can also include oligomers and polymers which are branched- or straight-chain species. In preferred embodiments, rigidity is imparted by the presence of cyclic groups (e.g., aryl, heteroaryl, cycloalkyl, heterocyclic, etc.). In other preferred embodiments, the ring is a six or ten member ring. In still further preferred embodiments, the ring is an aromatic ring such as, for example, phenyl or naphthyl.

Different hydrophobic/hydrophilic characteristics of the linker as well as the presence or absence of charged moieties can readily be controlled by the skilled artisan. For example, the hydrophobic nature of a linker derived from hexamethylene diamine ($H_2N(CH_2)_6NH_2$) or related polyamines can be modified to be substantially more hydrophilic by replacing the alkylene group with a poly(oxyalkylene) group such as found in the commercially available "Jeffamines".

Different frameworks can be designed to provide preferred orientations of the ligands. Such frameworks may be represented by using an array of dots (as shown below) wherein each dot may potentially be an atom, such as C, O, N, S, P, H, F, Cl, Br, and F or the dot may alternatively indicate the absence of an atom at that position. To facilitate the understanding of the framework structure, the framework is illustrated as a two dimensional array in the following diagram, although clearly the framework is a three dimensional array in practice:

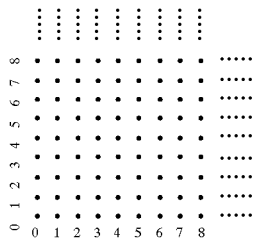

Each dot is either an atom, chosen from carbon, hydrogen, oxygen, nitrogen, sulfur, phosphorus, or halogen, or the dot represents a point in space (i.e., an absence of an atom). As is apparent to the skilled artisan, only certain atoms on the grid have the ability to act as an attachment point for the ligands, namely, C, O, N, S and P.

Atoms can be connected to each other via bonds (single, double or triple bonds with acceptable resonance and tautomeric forms), with regard to the usual constraints of chemical bonding. Ligands may be attached to the framework via single, double or triple bonds (with chemically acceptable tautomeric and resonance forms). Multiple ligand groups (2 to 10) can be attached to the framework such that the minimal, shortest path distance between adjacent ligand groups does not exceed 100 atoms. Preferably, the linker connections to the ligand is selected such that the maximum spatial distance between two adjacent ligands is no more than 100 Å.

An example of a linker as presented by the grid is shown below for a biphenyl construct.

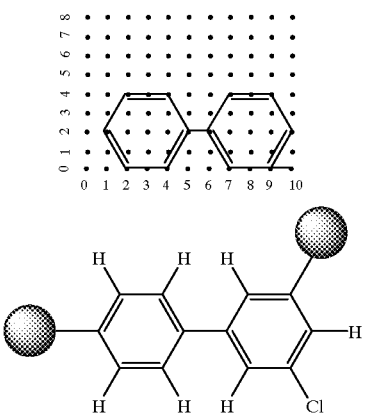

Nodes (1,2), (2,0), (4,4), (5,2), (4,0), (6,2), (7,4), (9,4), (10,2), (9,0), (7,0) all present carbon atoms. Node (10,0) represents a chlorine atom. All other nodes (or dots) are points in space (i.e., represent an absence of atoms).

Nodes (1,2) and (9,4) are attachment points. Hydrogen atoms are affixed to nodes (2,4), (4,4), (4,0), (2,0), (7,4), (10,2) and (7,0). Nodes (5,2) and (6,2) are connected by a single bond.

The carbon atoms present are connected by either a single or double bonds, taking into consideration the principle of resonance and/or tautomerism.

The intersection of the framework (linker) and the ligand group, and indeed, the framework (linker) itself can have many different bonding patterns. Examples of acceptable patterns of three contiguous atom arrangements are shown in the following diagram:

| CCC | NCC | OCC | SCC | PCC |
| CCN | NCN | OCN | SCN | PCN |
| CCO | NCO | OCO | SCO | PCO |
| CCS | NCS | OCS | SCS | PCS |
| CCP | NCP | OCP | SCP | PCP |
| | | | | |
| CNC | NNC | ONC | SNC | PNC |
| CNN | NNN | ONN | <u>SNN</u> | PNN |
| CNO | NNO | <u>ONO</u> | SNO | PNO |
| CNS | <u>NNS</u> | ONS | SNS | PNS |
| CNP | <u>NNP</u> | ONP | SNP | PNP |
| | | | | |
| COC | NOC | <u>OOC</u> | SOC | POC |
| <u>COO</u> | <u>NON</u> | <u>OON</u> | SON | PON |
| COC | <u>NOO</u> | <u>OOO</u> | <u>SOO</u> | <u>POO</u> |
| COP | <u>NOP</u> | <u>OOS</u> | <u>SOS</u> | <u>POS</u> |
| | | <u>OOP</u> | <u>SOP</u> | POP |
| CSC | NSC | | | |
| CSN | NSN | OSC | SSC | PSC |
| CSO | NSO | OSN | SSN | <u>PSN</u> |
| CSS | NSS | OSO | <u>SSO</u> | <u>PSO</u> |
| CSP | NSP | OSS | <u>SSS</u> | <u>PSS</u> |
| | | OSP | <u>SSP</u> | PSP |
| CPC | NPC | | | |
| CPN | NPN | OPC | SPC | <u>PPC</u> |
| CPO | NPO | OPN | SPN | <u>PPN</u> |
| CPS | NPS | OPO | SPO | <u>PPO</u> |
| <u>CPP</u> | <u>NPP</u> | OPS | SPS | <u>PPS</u> |
| | | OPP | SPP | PPP |

One skilled in the art would be able to identify bonding patterns that would produce multivalent compounds. Methods for producing these bonding arrangements are described in March, "Advanced Organic Chemistry", 4th Edition, Wiley-Interscience, New York, N.Y. (1992). These arrangements are described in the grid of dots shown in the scheme above. All of the possible arrangements for the five most preferred atoms are shown. Each atom has a variety of acceptable oxidation states. The bonding arrangements underlined are less acceptable and are not preferred.

Examples of molecular structures in which the above bonding patterns could be employed as components of the linker are shown below.

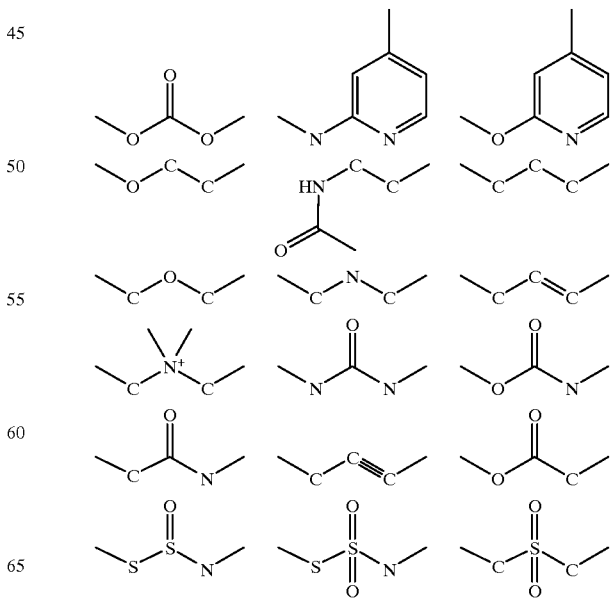

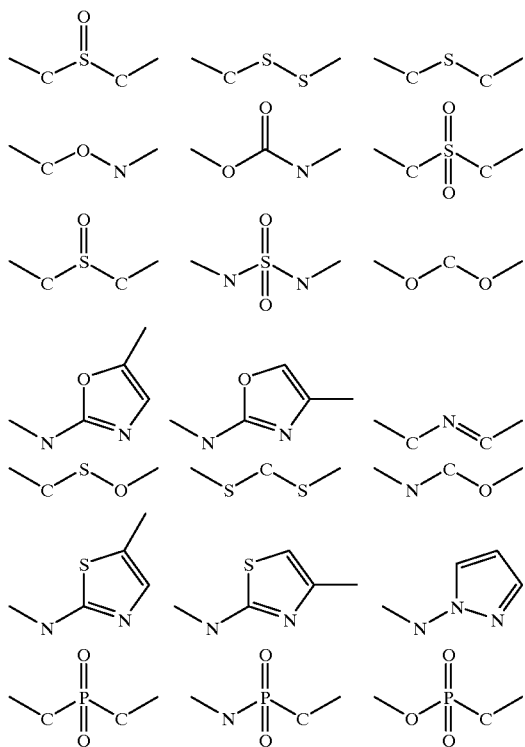

Figure 3:
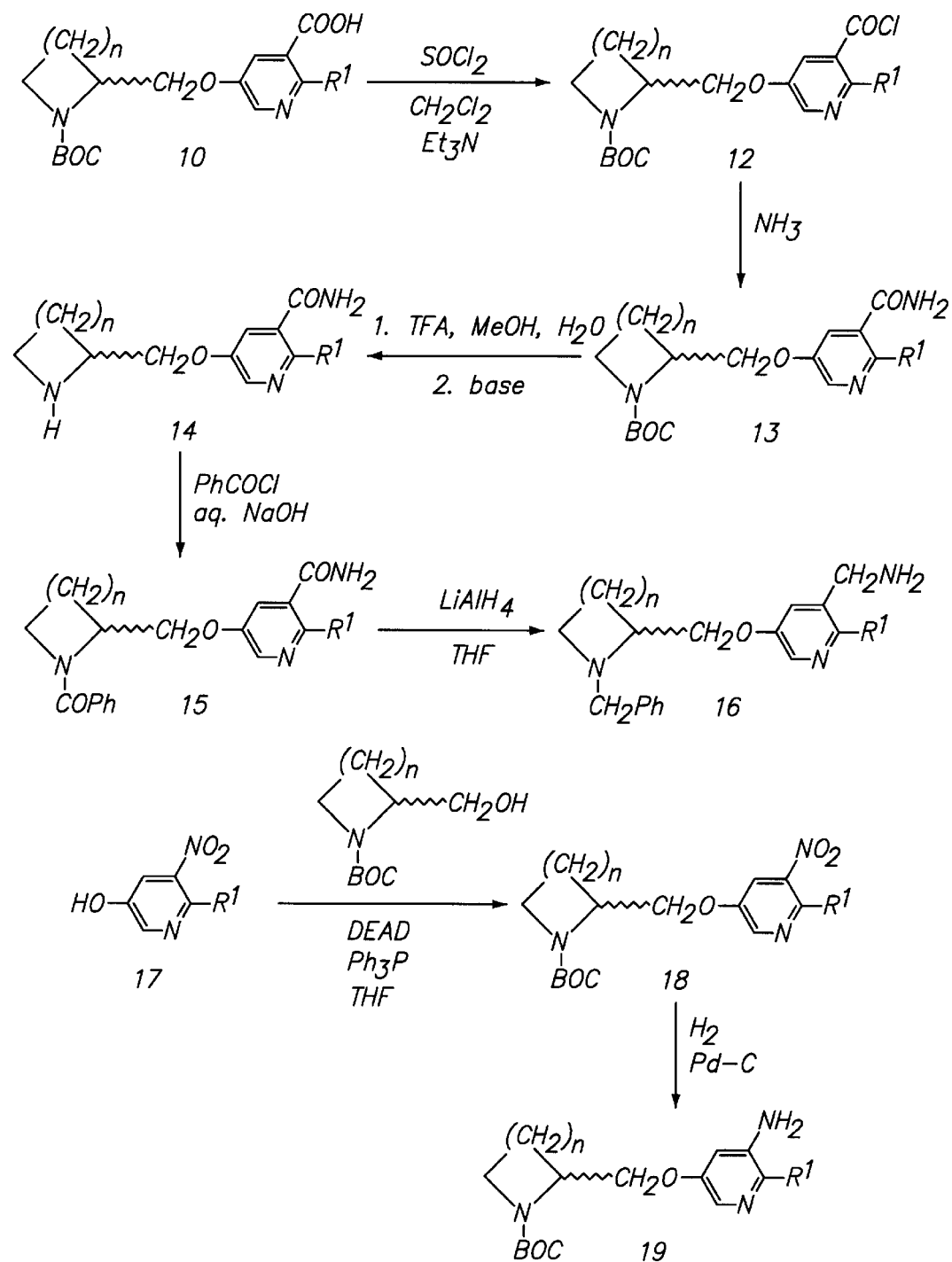

The identification Of an appropriate framework geometry and size for ligand domain presentation are important steps in the construction of a multibinding compound with enhanced activity. Systematic spatial searching strategies can be used to aid in the identification of preferred frameworks through an iterative process. FIG. 3 illustrates a useful strategy for determining an optimal framework display orientation for ligand domains. Various other strategies are known to those skilled in the art of molecular design and can be used for preparing compounds of this invention.

As shown in FIG. 3, display vectors around similar central core structures such as a phenyl structure (Panel A) and a cyclohexane structure (Panel B) can be varied, as can the spacing of the ligand domain from the core structure (i.e., the length of the attaching moiety). It is to be noted that core structures other than those shown here can be used for determining the optimal framework display orientation of the ligands. The process may require the use of multiple copies of the same central core structure or combinations of different types of display cores.

The above-described process can be extended to trimers (FIG. 2) and compound of higher valency.

Assays of each of the individual compounds of a collection generated as described above will lead to a subset of compounds with the desired enhanced activities (e.g., potency, selectivity, etc.). The analysis of this subset using a technique such as Ensemble Molecular Dynamics will provide a framework orientation that favors the properties desired. A wide diversity of linkers is commercially available (see, e.g., Available Chemical Directory (ACD)). Many of the linkers that are suitable for use in this invention fall into this category. Other can be readily synthesized by methods well known in the art and/or are described below.

Having selected a preferred framework geometry, the physical properties of the linker can be optimized by varying the chemical composition thereof. The composition of the linker can be varied in numerous ways to achieve the desired physical properties for the multibinding compound.

It can therefore be seen that there is a plethora of possibilities for the composition of a linker. Examples of linkers include aliphatic moieties, aromatic moieties, steroidal moieties, peptides, and the like. Specific examples are peptides or polyamides, hydrocarbons, aromatic groups, ethers, lipids, cationic or anionic groups, or a combination thereof.

Examples are given below, but it should be understood that various changes may be made and equivalents may be substituted without departing from the true spirit and scope of the invention. For example, properties of the linker can be modified by the addition or insertion of ancillary groups into or onto the linker, for example, to change the solubility of the multibinding compound (in water, fats, lipids, biological fluids, etc.), hydrophobicity, hydrophilicity, linker flexibility, antigenicity, stability, and the like. For example, the introduction of one or more poly(ethylene glycol) (PEG) groups onto or into the linker enhances the hydrophilicity and water solubility of the multibinding compound, increases both molecular weight and molecular size and, depending on the nature of the unPEGylated linker, may increase the in vivo retention time. Further PEG may decrease antigenicity and potentially enhances the overall rigidity of the linker.

Ancillary groups which enhance the water solubility/hydrophilicity of the linker and, accordingly, the resulting multibinding compounds are useful in practicing this invention. Thus, it is within the scope of the present invention to use ancillary groups such as, for example, small repeating units of ethylene glycols, alcohols, polyols (e.g., glycerin, glycerol propoxylate, saccharides, including mono-, oligosaccharides, etc.), carboxylates (e.g., small repeating units of glutamic acid, acrylic acid, etc.), amines (e.g., tetraethylenepentamine), and the like) to enhance the water solubility and/or hydrophilicity of the multibinding compounds of this invention. In preferred embodiments, the ancillary group used to improve water solubility/hydrophilicity will be a polyether.

The incorporation of lipophilic ancillary groups within the structure of the linker to enhance the lipophilicity and/or hydrophobicity of the multibinding compounds described herein is also within the scope of this invention. Lipophilic groups useful with the linkers of this invention include, by way of example only, aryl and heteroaryl groups which, as above, may be either unsubstituted or substituted with other groups, but are at least substituted with a group which allows their covalent attachment to the linker. Other lipophilic groups useful with the linkers of this invention include fatty acid derivatives which do not form bilayers in aqueous medium until higher concentrations are reached.

Also within the scope of this invention is the use of ancillary groups which result in the multibinding compound being incorporated or anchored into a vesicle or other membranous structure such as a liposome or a micelle. The term "lipid" refers to any fatty acid derivative that is capable of forming a bilayer or a micelle such that a hydrophobic portion of the lipid material orients toward the bilayer while a hydrophilic portion orients toward the aqueous phase. Hydrophilic characteristics derive from the presence of phosphate, carboxylic, sulfato, amino, sulfhydryl, nitro and other like groups well known in the art. Hydrophobicity could be conferred by the inclusion of groups that include, but are not limited to, long chain saturated and unsaturated aliphatic hydrocarbon groups of up to 20 carbon atoms and such groups substituted by one or more aryl, heteroaryl, cycloalkyl, and/or heterocyclic group(s). Preferred lipids are phosphaglycerides and sphingolipids, representative examples of which include phosphatidylcholin, phosphatidylethanolamine, phosphatidylserine, phosphatidylinositol, phosphatidic acid, palmitoyleoyl phosphatidylcholine, lysophosphatidylcholine, lysophosphatidyl-ethanolamine, dipalmitoylphosphatidyl-choline, dioleoylphosphatidylcholine, distearoyl-phosphatidylcholine or dilinoleoylphosphatidylcholine could be used. Other compounds lacking phosphorus, such as sphingolipid and glycosphingolipid families are also within the group designated as lipid. Additionally, the amphipathic lipids described above may be mixed with other lipids including triglycerides and sterols.

The flexibility of the linker can be manipulated by the inclusion of ancillary groups which are bulky and/or rigid. The presence of bulky or rigid groups can hinder free rotation about bonds in the linker or bonds between the linker and the ancillary group(s) or bonds between the linker and the functional groups. Rigid groups can include, for example, those groups whose conformational lability is restrained by the presence of rings and/or multiple bonds within the group, for example, aryl, heteroaryl, cycloalkyl, cycloalkenyl, and heterocyclic groups. Other groups which can impart rigidity include polypeptide groups such as oligo- or polyproline chains.

Rigidity can also be imparted electrostatically. Thus, if the ancillary groups are either positively or negatively charged, the similarly charged ancillary groups will force the presenter linker into a configuration affording the maximum distance between each of the like charges. The energetic cost of bringing the like-charged groups closer to each other will tend to hold the linker in a configuration that maintains the separation between the like-charged ancillary groups. Further ancillary groups bearing opposite charges will tend to be attracted to their oppositely charged counterparts and potentially may enter into both inter- and intramolecular ionic bonds. This non-covalent mechanism will tend to hold the linker into a conformation which allows bonding between the oppositely charged groups. The addition of ancillary groups which are charged, or alternatively, bear a latent charge when deprotected, following addition to the linker, include deprotonation of a carboxyl, hydroxyl, thiol or amino group by a change in pH, oxidation, reduction or other mechanisms known to those skilled in the art which result in removal of the protecting group, is within the scope of this invention.

Rigidity may also be imparted by internal hydrogen bonding or by hydrophobic collapse.

Bulky groups can include, for example, large atoms, ions (e.g., iodine, sulfur, metal ions, etc.) or groups containing large atoms, polycyclic groups, including aromatic groups, non-aromatic groups and structures incorporating one or more carbon-carbon multiple bonds (i.e., alkenes and alkynes). Bulky groups can also include oligomers and polymers which are branched- or straight-chain species. Species that are branched are expected to increase the rigidity of the structure more per unit molecular weight gain than are straight-chain species.

In preferred embodiments, rigidity is imparted by the presence of cyclic groups (e.g., aryl, heteroaryl, cycloalkyl, heterocyclic, etc.). In other preferred embodiments, the linker comprises one or more six-membered rings. In still further preferred embodiments, the ring is an aryl group such as, for example, phenyl or naphthyl.

In view of the above, it is apparent that the appropriate selection of a linker group providing suitable orientation, restricted/unrestricted rotation, the desired degree of hydrophobicity/hydrophilicity, etc. is well within the skill of the art. Eliminating or reducing antigenicity of the multibinding compounds described herein is also within the scope of this invention. In certain cases, the antigenicity of a multibinding compound may be eliminated or reduced by use of groups such as, for example, poly(ethylene glycol).

As explained above, the multibinding compounds described herein comprise 2–10 ligands attached to a linker that attaches the ligands in such a manner that they are presented to the enzyme for multivalent interactions with ligand binding sites thereon/therein. The linker spatially constrains these interactions to occur within dimensions defined by the linker. This and other factors increases the biological activity of the multibinding compound as compared to the same number of ligands made available in monobinding form.

The compounds of this invention are preferably represented by the empirical Formula $(L)_p(X)_q$ where L, X, p and q are as defined above. This is intended to include the several ways in which the ligands can be linked together in order to achieve the objective of multivalency, and a more detailed explanation is described below.

As noted previously, the linker may be considered as a framework to which ligands are attached. Thus, it should be recognized that the ligands can be attached at any suitable position on this framework, for example, at the termini of a linear chain or at any intermediate position.

The simplest and most preferred multibinding compound is a bivalent compound which can be represented as L—X—L, where each L is independently a ligand which may be the same or different and each X is independently the linker. Examples of such bivalent compounds are provided in FIG. 1 where each shaded circle represents a ligand. A trivalent compound could also be represented in a linear fashion, i.e., as a sequence of repeated units L—X—L—X—L, in which L is a ligand and is the same or different at each occurrence, as can X. However, a trimer can also be a radial multibinding compound comprising three ligands attached to a central core, and thus represented as $(L)_3X$, where the linker X could include, for example, an aryl or cycloalkyl group. Illustrations of trivalent and tetravalent compounds of this invention are found in FIGS. 2 and 3 respectively where, again, the shaded circles represent ligands. Tetravalent compounds can be represented in a linear array, e.g.,

L—X—L—X—L—X—L in a branched array, e.g.,

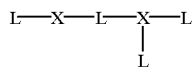

(a branched construct analogous to the isomers of butane—n-butyl, iso-butyl, sec-butyl, and t-butyl) or in a tetrahedral array, e.g.,

where X and L are as defined herein. Alternatively, it could be represented as an alkyl, aryl or cycloalkyl derivative as above with four (4) ligands attached to the core linker.

Figure 4A:
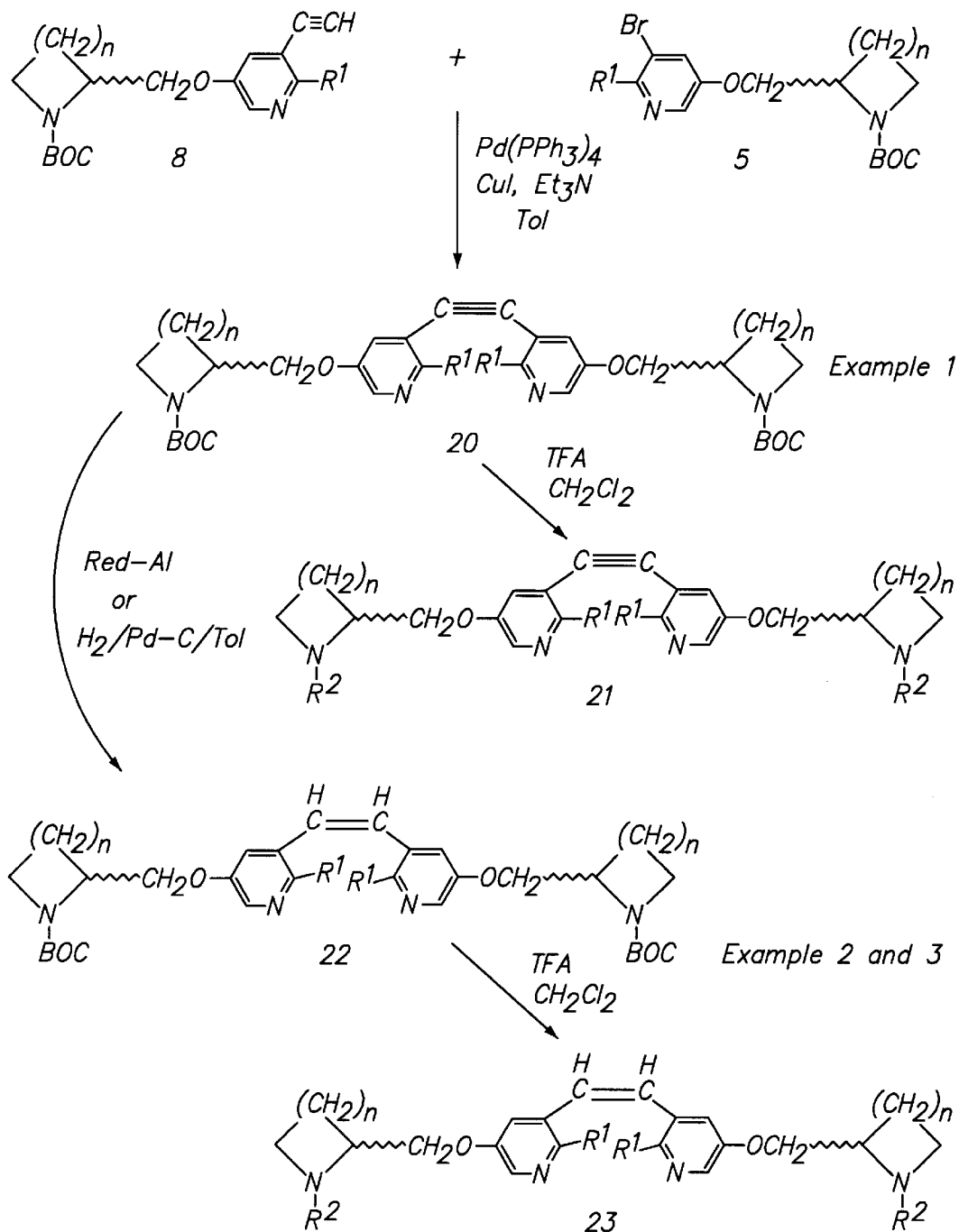
Figure 4B:
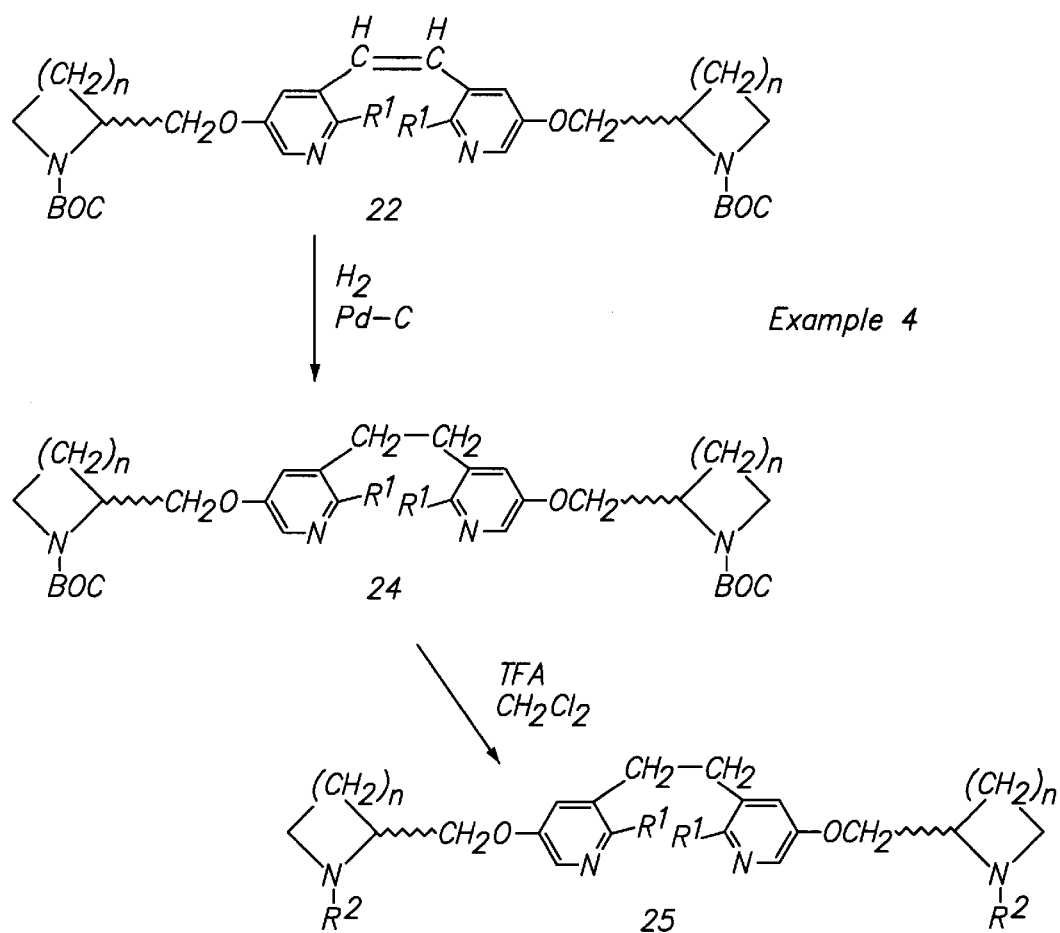
Figure 5:
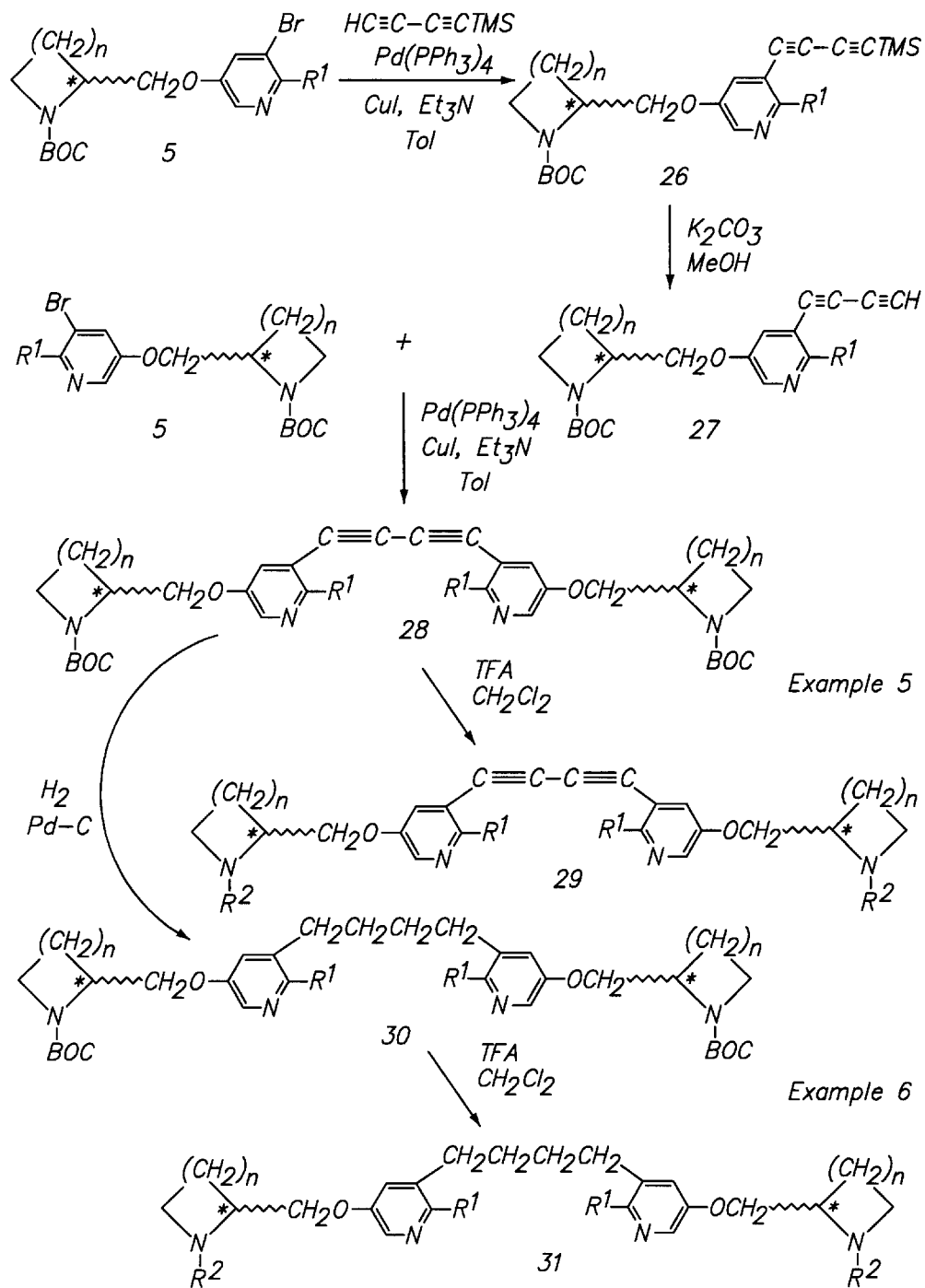
Figure 6:
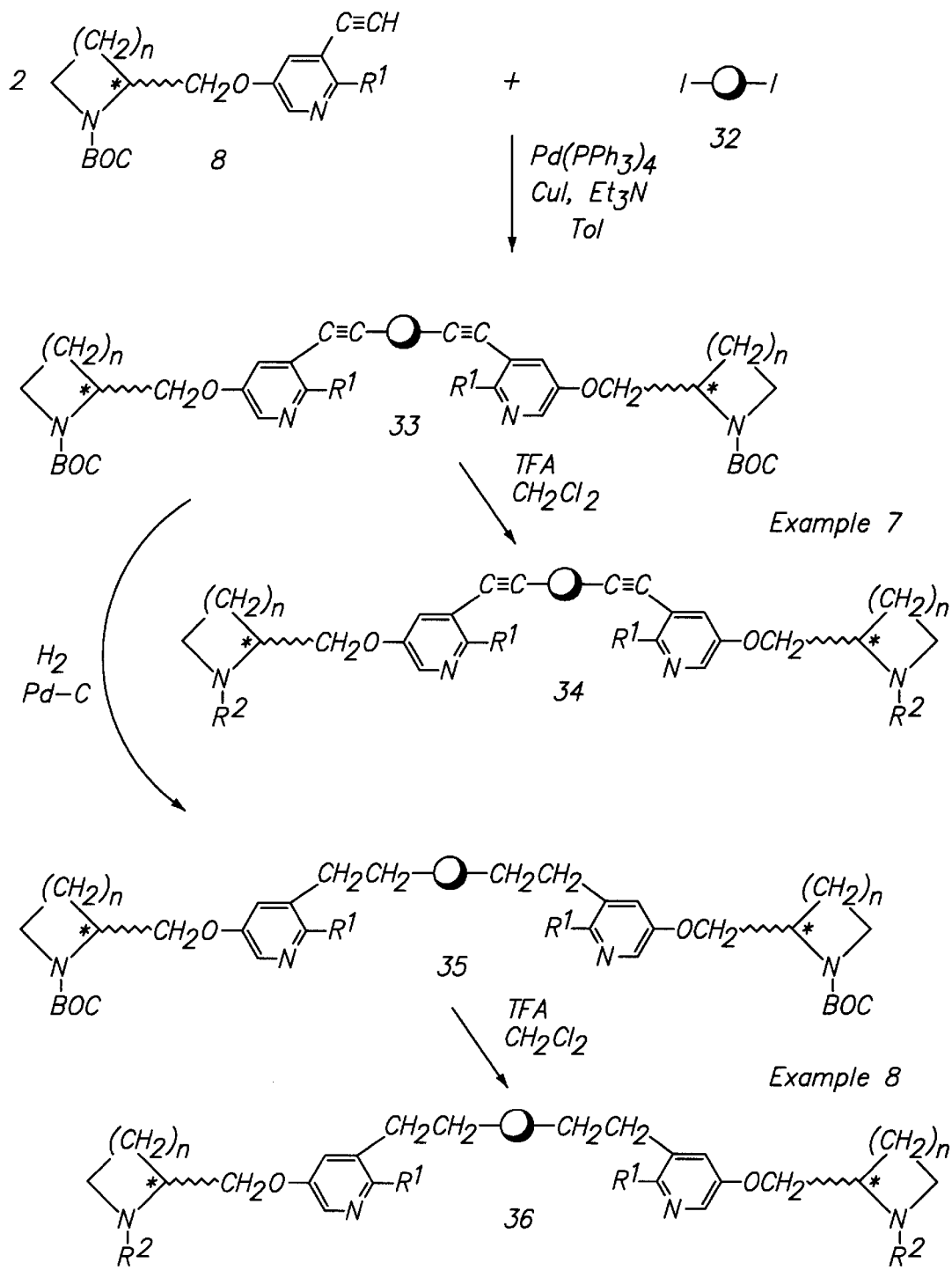
Figure 7:
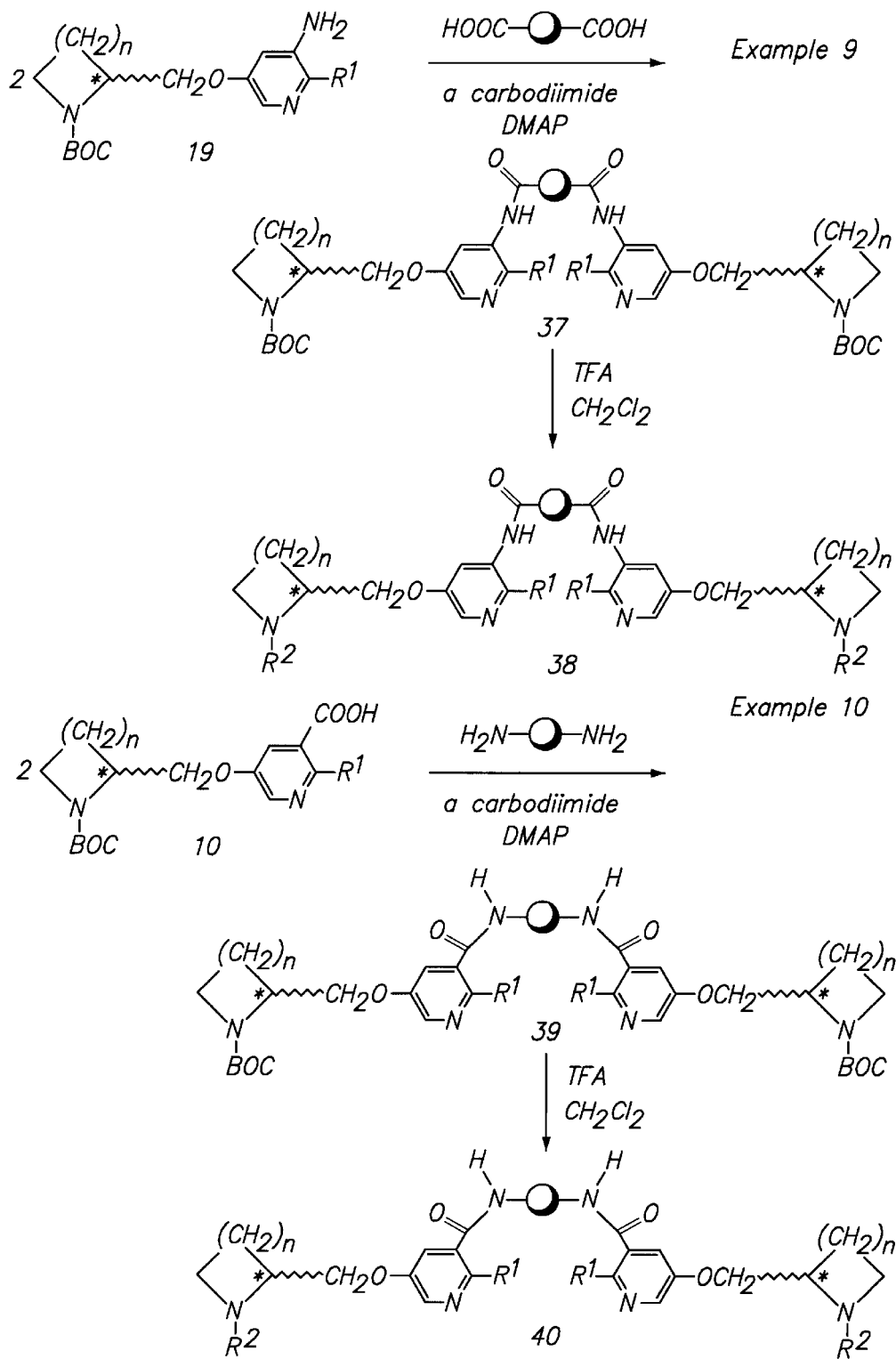

The same considerations apply to higher multibinding compounds of this invention containing 5–10 ligands as illustrated in FIG. 4 where, as before, the shaded circles represent ligands. However, for multibinding agents attached to a central linker such as aryl or cycloalkyl, there is a self-evident constraint that there must be sufficient attachment sites on the linker to accommodate the number of ligands present; for example, a benzene ring could not directly accommodate more than 6 ligands, whereas a multi-ring linker (e.g., biphenyl) could accommodate a larger number of ligands.

Certain of the above described compounds may alternatively be represented as cyclic chains of the form:

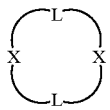

and variants thereof.

All of the above variations are intended to be within the scope of the invention defined by the Formula $(L)_p(X)_q$.

In view of the above description of the linker, it is understood that the term "linker" when used in combination with the term "multibinding compound" includes both a covalently contiguous single linker (e.g., L—X—L) and multiple covalently non-contiguous linkers (L—X—L—X—L) within the multibinding compound.

The preferred linker length will vary depending upon the distance between adjacent ligand recognition sites, and the geometry, flexibility and composition of the linker. The length of the linker will preferably be in the range of about 2–100 Angstroms, more preferably about 2–50 Angstroms, and even more preferably about 3–20 Angstroms.

With the foregoing in mind, preferred linkers may be represented by the following formula:

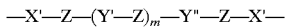

in which:

m is an integer of 0–20;

X' at each separate occurrence is —O—, —S—, —S(O)—, —S(O)$_2$—, —NR— (where R is as defined below), —C(O)—, or a covalent bond;

Z at each separate occurrence is alkylene, cycloalkylene, alkenylene, alkynylene, arylene, heteroarylene, or a covalent bond;

Y' and Y' at each separate occurrence are

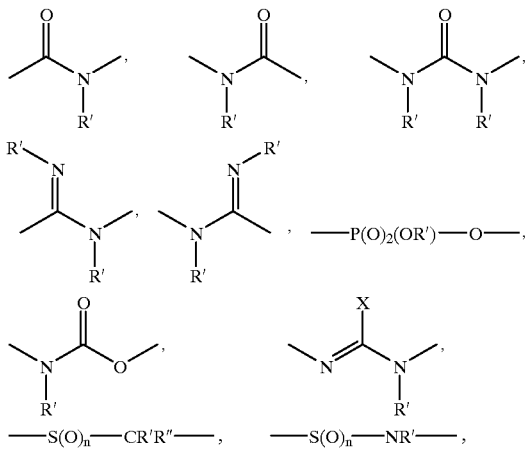

S—S—, or a covalent bond;
in which:
n is 0, 1 or 2; and

R, R' and R" at each separate occurrence are chosen from hydrogen, alkyl, cycloalkyl, alkenyl, cycloalkenyl, alkynyl, aryl, heteroaryl, and heterocyclo.

Additionally, the linker moiety can be optionally substituted at any atom in the chain by alkyl, cycloalkyl, alkenyl, alkynyl, alkoxy, halo, nitro, aryl, heteroaryl, or heterocyclo.

UTILITY

The multibinding agents of the invention are useful in medical treatments related to the modulation of to nicotinic acetylcholine receptors, and accordingly exhibit biological effects well known to those skilled in the art. Examples of such activity include the alleviation of pain, resulting from variety of pathological states such as migraine, headache, inflammatory disease, and the like.

TESTING

The multibinding agents of the invention are useful in medical treatments and exhibit biological effects that can be demonstrated in routine tests well known to those skilled in the art. For example, assessment of analgesic effect can be studied in models of nociceptive pain such as the early phase formalin test (1), thermally induced paw withdrawal (2), thermally-induced tail flick (3). Neuropathic pain can be evaluated in models of neuropathic injury induced by constriction of primary afferent neurons (4), spinal nerve ligation (5), or partial nerve transection (6). The analgesic effect of the invention on persistent pain may be evaluated in animals treated with formalin (7). In addition, the interaction of the ligand with receptor may be directly evaluated in vitro (8). (See, Appendix 1).

Combinatorial Libraries

The methods described above lend themselves to combinatorial approaches for selecting compounds that have multibinding properties related to the nicotinic acetylcholine receptor (nAChR), from a library of multimeric compounds.

Specifically, factors such as the proper juxtaposition of the individual nAChR-binding ligands of a multibinding compound with respect to the relevant array of binding sites on a target or targets is important in optimizing the interaction of the multibinding compound with its target(s) and to maximize the biological advantage through multivalency. One approach is to identify a library of candidate multibinding compounds with properties spanning the multibinding parameters that are relevant for a particular target. These parameters include: (1) the identity of ligand(s), (2) the orientation of ligands, (3) the valency of the construct, (4) linker length, (5) linker geometry, (6) linker physical properties, and (7) linker chemical functional groups.

Libraries of multimeric compounds potentially possessing multibinding properties (i.e., candidate multibinding compounds) and comprising a multiplicity of such variables are prepared and these libraries are then evaluated via conventional assays corresponding to the ligand selected and the multibinding parameters desired. Considerations relevant to each of these variables are set forth below:

Selection of Ligand(s)

A single nAChR-binding ligand or set of nAChR-binding ligands is (are) selected for incorporation into the libraries of candidate multibinding compounds. The only requirement for the ligands chosen is that they are capable of interacting with an nAChR. Thus, nAChR-binding ligands may be known drugs, modified forms of known drugs, substructures of known drugs or substrates of modified forms of known drugs (which are competent to interact with the target), or other compounds. nAChR-binding ligands are preferably chosen based on known favorable properties that may be projected to be carried over to or amplified in multibinding forms. Favorable properties include demonstrated safety and efficacy in human patients, appropriate PK/ADME profiles, synthetic accessibility, and desirable physical properties such as solubility, logP, etc. However, it is crucial to note that nAChR-binding ligands which display an unfavorable property from among the previous list may obtain a more favorable property through the process of multibinding compound formation; i.e., nAChR-binding ligands should not necessarily be excluded on such a basis. For example, an nAChR-binding ligand that is not sufficiently potent at a particular target so as to be efficacious in a human patient may become highly potent and efficacious when presented in multibinding form. An nAChR-binding ligand that is potent and efficacious but not of utility because of a non-mechanism-related toxic side effect may have increased therapeutic index (increased potency relative to toxicity) as a multibinding compound. Compounds that exhibit short in vivo half-lives may have extended half-lives as multibinding compounds. Physical properties of nAChR-binding ligands that limit their usefulness (e.g. poor bioavailability due to low solubility, hydrophobicity, hydrophilicity) may be rationally modulated in multibinding forms, providing compounds with physical properties consistent with the desired utility.

Orientation: Selection of nAChR-binding Ligand Attachment Points and Linking Chemistry Several points are chosen on each nAChR-binding ligand at which to attach the nAChR-binding ligand to the linker. The selected points on the nAChR-binding ligand/linker for attachment are functionalized to contain complementary reactive functional groups. This permits probing the effects of presenting the nAChR-binding ligands to their receptor(s) in multiple relative orientations, an important multibinding design parameter. The only requirement for choosing attachment points is that attaching to at least one of these points does not abrogate activity of the nAChR-binding ligand. Such points for attachment can be identified by structural information when available. For example, inspection of a co-crystal structure of a protease inhibitor bound to its target allows one to identify one or more sites where linker attachment will not preclude the enzyme:inhibitor interaction. Alternatively, evaluation of ligand/target binding by nuclear magnetic resonance will permit the identification of sites non-essential for ligand/target binding. See, for example, Fesik, et al., U.S. Pat. No. 5,891,643. When such structural information is not available, utilization of structure-activity relationships (SAR) for ligands will suggest positions where substantial structural variations are and are not allowed. In the absence of both structural and SAR information, a library is merely selected with multiple points of attachment to allow presentation of the nAChR-binding ligand in multiple distinct orientations. Subsequent evaluation of this library will indicate what positions are suitable for attachment.

It is important to emphasize that positions of attachment that do abrogate the activity of the monomeric nAChR-binding ligand may also be advantageously included in candidate multibinding compounds in the library provided that such compounds bear at least one nAChR-binding ligand attached in a manner which does not abrogate intrinsic activity. This selection derives from, for example, heterobivalent interactions within the context of a single target molecule. For example, consider an nAChR-binding ligand bound to its target receptor, and then consider modifying this ligand by attaching to it a second copy of the same ligand with a linker which allows the second ligand to interact with the same receptor molecule at sites proximal to the antagonist binding site, which include elements of the receptor that are not part of the formal antagonist binding site and/or elements of the matrix surrounding the receptor such as the membrane. Here, the most favorable orientation for interaction of the second ligand molecule with the receptor/matrix may be achieved by attaching it to the linker at a position which abrogates activity of the nAChR-binding ligand at the formal agonist binding site. Another way to consider this is that the SAR of individual nAChR-binding ligands within the context of a multibinding structure is often different from the SAR of those same ligands in monomeric form.

The foregoing discussion focused on bivalent interactions of dimeric compounds bearing two copies of the same nAChR-binding ligand joined to-a single linker through different attachment points, one of which may abrogate the binding/activity of the monomeric nAChR-binding ligand. It should also be understood that bivalent advantage may also be attained with heterodimeric constructs bearing two different nAChR-binding ligands, which may be agonists or antagonists, that bind to common or different targets.

Once the nAChR-binding ligand attachment points have been chosen, one identifies the types of chemical linkages that are possible at those points. The most preferred types of chemical linkages are those that are compatible with the overall structure of the nAChR-binding ligand (or protected forms of the nAChR-binding ligand) readily and generally formed, stable and intrinsically innocuous under typical chemical and physiological conditions, and compatible with a large number of available linkers. Amide bonds, ethers, amines, carbamates, ureas, and sulfonamides are but a few examples of preferred linkages.

Linkers: Spanning Relevant Multibinding Parameters Through Selection of Valency, Linker Length, Linker Geometry, Rigidity, Physical Properties, and Chemical Functional Groups In the library of linkers employed to generate the library of candidate multibinding compounds, the selection of linkers employed in this library of linkers takes into consideration the following factors:

Valency

In most instances the library of linkers is initiated with divalent linkers. The choice of nAChR-binding ligands and proper juxtaposition of two nAChR-binding ligands relative to their binding sites permits such molecules to exhibit target binding affinities and specificities more than sufficient to confer biological advantage. Furthermore, divalent linkers or constructs are also typically of modest size such that they retain the desirable biodistribution properties of small molecules.

Linker Length

Linkers are chosen in a range of lengths to allow the spanning of a range of inter-ligand distances that encompass the distance preferable for a given divalent interaction. In some instances the preferred distance can be estimated rather precisely from high-resolution structural information of targets, typically enzymes and soluble receptor targets. In other instances where high-resolution structural information is not available (such as 7TM G-protein coupled receptors), one can make use of simple models to estimate the maximum distance between binding sites either on adjacent receptors or at different locations on the same receptor. In situations where two binding sites are present on the same target (or target subunit for multisubunit targets), preferred linker distances are 2–20 angstroms, with more preferred linker distances of 3–12 angstroms. In situations where two binding sites reside on separate (e.g., protein) target sites, preferred linker distances are 20–100 angstroms, with more preferred distances of 30–70 angstroms.

Linker Geometry and Rigidity

The combination of nAChR-binding ligand attachment site, linker length, linker geometry, and linker rigidity determine the possible ways in which the nAChR-binding ligands of candidate multibinding compounds may be displayed in three dimensions and thereby presented to their binding sites. Linker geometry and rigidity are nominally determined by chemical composition and bonding pattern, which may be controlled and are systematically varied as another spanning function in a multibinding array. For example, linker geometry is varied by attaching two nAChR-binding ligands to the ortho, meta, and para positions of a benzene ring, or in cis- or trans-arrangements at the 1,1- vs. 1,2- vs. 1,3- vs. 1,4-positions around a cyclohexane core or in cis- or trans-arrangements at a point of ethylene unsaturation. Linker rigidity is varied by controlling the number and relative energies of different conformational states possible for the linker. For example, a divalent compound bearing two nAChR-binding ligands joined by 1,8-octyl linker has many more degrees of freedom, and is therefore less rigid than a compound in which the two nAChR-binding ligands are attached to the 4,4' positions of a biphenyl linker.

Linker physical properties

The Physical Properties of Linkers are nominally determined by the chemical constitution and bonding patterns of the linker, and linker physical properties impact the overall physical properties of the candidate multibinding compounds in which they are included. A range of linker compositions is typically selected to provide a range of physical properties (hydrophobicity, hydrophilicity, amphiphilicity, polarization, acidity, and basicity) in the candidate multibinding compounds. The particular choice of linker physical properties is made within the context of the physical properties of the nAChR-binding ligands they join and preferably the goal is to generate molecules with favorable PK/ADME properties. For example, linkers can be selected to avoid those that are too hydrophilic or too hydrophobic to be readily absorbed and/or distributed in vivo.

Linker Chemical Functional Groups

Linker chemical functional groups are selected to be compatible with the chemistry chosen to connect linkers to the nAChR-binding ligands and to impart the range of physical properties sufficient to span initial examination of this parameter.

Combinatorial Synthesis

Having chosen a set of n nAChR-binding ligands (n being determined by the sum of the number of different attachment points for each nAChR-binding ligand chosen) and m linkers by the process outlined above, a library of (n!)m candidate divalent multibinding compounds is prepared which spans the relevant multibinding design parameters for a particular target. For example, an array generated from two nAChR-binding ligands, one which has two attachment points (A1, A2) and one which has three attachment points (B1, B2, B3) joined in all possible combinations provide for at least 15 possible combinations of multibinding compounds:

| | | | | | | | |
|---|---|---|---|---|---|---|---|
| A1-A1 | A1-A2 | A1-B1 | A1-B2 | A1-B3 | A2-A2 | A2-B1 | A2-B2 |
| A2-B3 | B1-B1 | B1-B2 | B1-B3 | B2-B2 | B2-B3 | B3-B3 | |

When each of these combinations is joined by 10 different linkers, a library of 150 candidate multibinding compounds results.

Given the combinatorial nature of the library, common chemistries are preferably used to join the reactive functionalities on the nAChR-binding ligands with complementary reactive functionalities on the linkers. The library therefore lends itself to efficient parallel synthetic methods. The combinatorial library can employ solid phase chemistries well known in the art wherein the nAChR-binding ligand and/or linker is attached to a solid support. Alternatively and preferably, the combinatorial library is prepared in the solution phase. After synthesis, candidate multibinding compounds are optionally purified before assaying for activity by, for example, chromatographic methods (e.g., HPLC).

Analysis of Array by Biochemical, Analytical, Pharmacological, and Computational Methods Various methods are used to characterize the properties and activities of the candidate multibinding compounds in the library to determine which compounds possess multibinding properties. Physical constants such as solubility under various solvent conditions and logD/clogD values can be determined. A combination of NMR spectroscopy and computational methods is used to determine low-energy conformations of the candidate multibinding compounds in fluid media. The ability of the members of the library to bind to the desired target and other targets is determined by various standard methods, which include radioligand displacement assays for receptor and ion channel targets, and kinetic inhibition analysis for many enzyme targets. In vitro efficacy, such as for receptor agonists and antagonists, ion channel blockers, and antimicrobial activity, can also be determined. Pharmacological data, including oral absorption, everted gut penetration, other pharmacokinetics parameters and efficacy data can be determined in appropriate models. In this way, key structure-activity relationships are obtained for multibinding design parameters which are then used to direct future work.

The members of the library which exhibit multibinding properties, as defined herein, can be readily determined by conventional methods. First those members which exhibit multibinding properties are identified by conventional methods as described above including conventional assays (both in vitro and in vivo).

Second, ascertaining the structure of those compounds which exhibit multibinding properties can be accomplished via art recognized procedures. For example, each member of the library can be encrypted or tagged with appropriate information allowing determination of the structure of relevant members at a later time. See, for example, Dower, et al., International Patent Application Publication No. WO 93/06121; Brenner, et al., Proc. Natl. Acad. Sci., USA, 89:5181 (1992); Gallop, et al., U.S. Pat. No. 5,846,839; each of which are incorporated herein by reference in its entirety. Alternatively, the structure of relevant multivalent compounds can also be determined from soluble and untagged libraries of candidate multivalent compounds by methods known in the art such as those described by Hindsgaul, et al., Canadian Patent Application No. 2,240,325 which was published on Jul. 11, 1998. Such methods couple frontal affinity chromatography with mass spectroscopy to determine both the structure and relative binding affinities of candidate multibinding compounds to receptors.

The process set forth above for dimeric candidate multibinding compounds can, of course, be extended to trimeric candidate compounds and higher analogs thereof.

Follow-up Synthesis and Analysis of Additional Array(s)

Based on the information obtained through analysis of the initial library, an optional component of the process is to ascertain one or more promising multibinding "lead" compounds as defined by particular relative nAChR-binding ligand orientations, linker lengths, linker geometries, etc. Additional libraries can then be generated around these leads to provide for further information regarding structure to activity relationships. These arrays typically bear more focused variations in linker structure in an effort to further optimize target affinity and/or activity at the target (antagonism, partial agonism, etc.), and/or alter physical properties. By iterative redesign/analysis using the novel principles of multibinding design along with classical medicinal chemistry, biochemistry, and pharmacology approaches, one is able to prepare and identify optimal multibinding compounds that exhibit biological advantage towards their targets and as therapeutic agents.

To further elaborate upon this procedure, suitable divalent linkers include, by way of example only, those derived from dicarboxylic acids, disulfonylhalides, dialdehydes, diketones, dihalides, diisocyanates, diamines, diols, mixtures of carboxylic acids, sulfonylhalides, aldehydes, ketones, halides, isocyanates, amines and diols. In each case, the carboxylic acid, sulfonylhalide, aldehyde, ketone, halide, isocyanate, amine and diol functional group is reacted with a complementary functionality on the nAChR-binding ligand to form a covalent linkage.

Exemplary linkers include those described in the Appendix.

PHARMACEUTICAL FORMULATIONS

When employed as pharmaceuticals, the compounds of the invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions that contain, as the active ingredient, one or more of the compounds of formula I above associated with one or more pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.1 mg to about 1 g, more usually about 1 to about 100 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

EXAMPLES

The following preparations and examples are given to enable those skilled in the art to more clearly understand and to practice the present invention. They should not be considered as limiting the scope of the invention, but merely as being illustrative and representative thereof.

In the examples below, the following abbreviations have the following meanings. Unless otherwise stated, all temperatures are in degrees Celsius. If an abbreviation is not defined, it has its generally accepted meaning.

Å=Angstroms
cm=centimeter
DCC=dicyclohexyl carbodiumide
DMF=N,N-dimethylformamide
DMSO=dimethylsulfoxide
g=gram
HPLC=high performance liquid chromatography
MEM=minimal essential medium
mg=milligram
MIC=minimum inhibitory concentration
min=minute
mL=milliliter
mm=millimeter
mmol=millimol
N=normal
THF=tetrahydrofuran
μL=microliters
μm=microns
rt=room temperature
Rf=retention factor
NMR=nuclear magnetic resonance
ESMS=ekectrospray mass spectrum
ppm=parts per million Example 1

Figure 8:
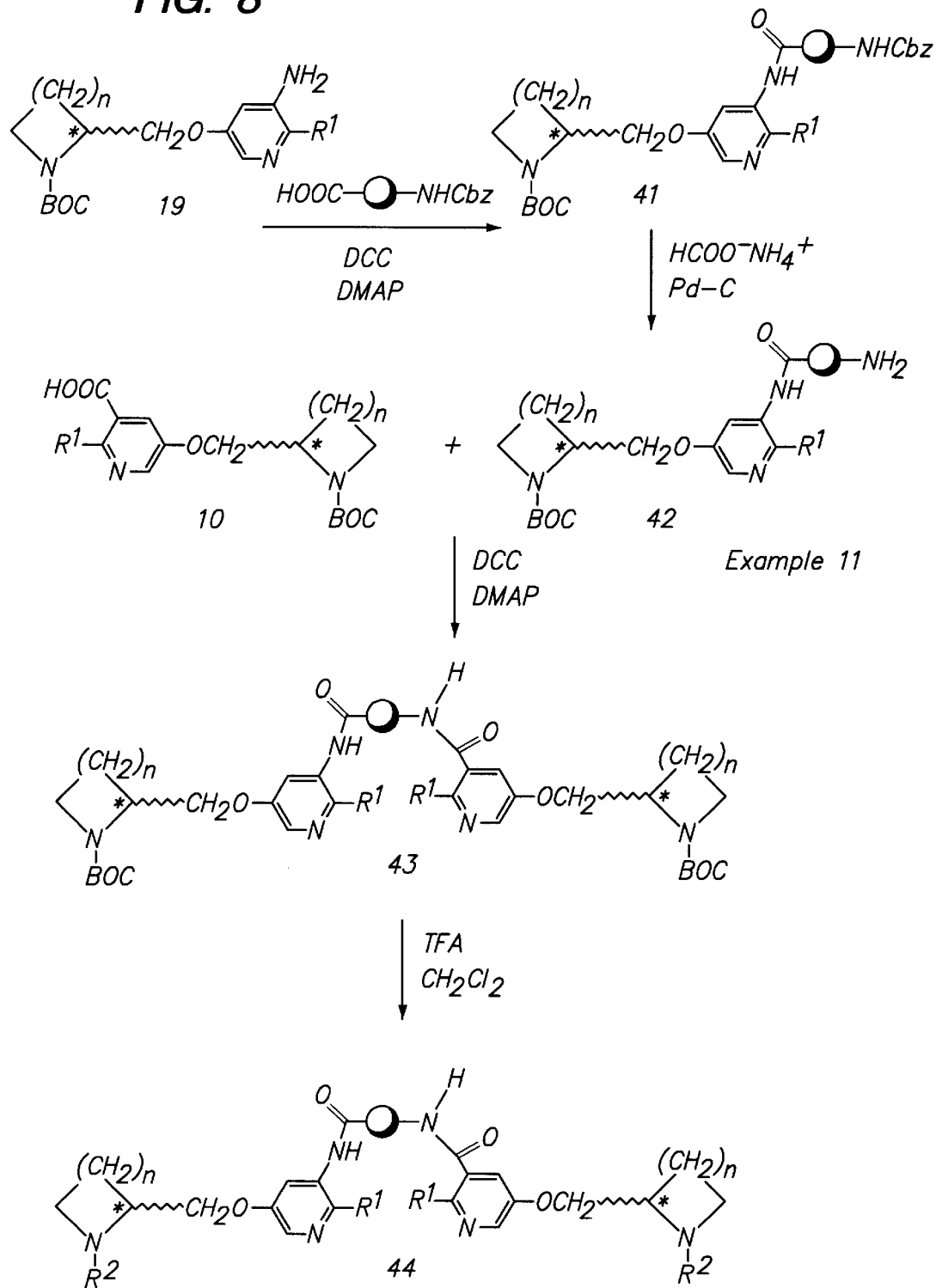

Following FIG. 8
Preparation of a Formula I Compound Wherein p is 2, q is 1, and Each Ligand, L, is (S)-2-chloro-5-(2-azetidinylmethoxy)pyridine and the Linker, X, is an Acetylenic Bond

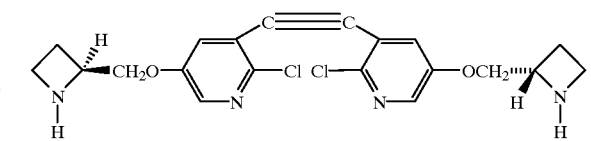

Step 1
A solution of (S)-2-chloro-3-ethynyl-5-(2-azetidinylmethoxy)pyridine (compound 8 where $R^1$=Cl and n =1, prepared as described in PCT Application Publication No. WO 98/25920, example 30) (1 mmol), (S)-2-chloro-3-bromo-5-(2-azetidinylmethoxy)-pyridine (compound 5 where $R^1$=Cl and n=1, prepared as described in PCT Application Publication No. WO 98/25920, example 26) (1 mmol), tetrakis(triphenylphosphine)palladium(0) (150 mg), and triethylamine (0.3 mL) in toluene (10 mL) is stirred with copper (I) iodide (20 mg). The mixture is stirred at 100° C. and the progress of the reaction is followed by thin layer chromatography (tlc). After reaction is complete, the mixture is cooled, filtered, and the solvent is removed under reduced pressure to give the crude reaction product. The desired compound 20 (where $R^1$=Cl and n=1) is obtained by purification of the crude product with the use of HPLC.

Step 2
A solution of compound 20 from step 1 above, and trifluoroacetic acid (3 mL) in $CH_2Cl_2$ (5 mL) is stirred at room temperature. The progress of the reaction is followed by tlc. After the reaction is complete, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 21 where $R^1$=Cl, $R^2$=H, n=1) is obtained by purification of the crude product with the use of HPLC.

Note that by choice of a compound of structure 8 having $R^1$ and/or n different from those of the compound of structure 5, a compound of Formula I having two different ligands, L, is prepared.

Example 2

Following FIG. 8
Preparation of a Formula I Compound Wherein p is 2, q is 1, and Each L is (S)-2-chloro-5-(2-axetidinylmethoxy) pyridine and the Linker, X, is a trans Ethylenic Bond

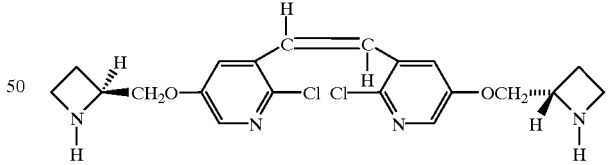

Step 1
A solution of the compound 20 (where $R^1$=Cl and n=1, prepared as described in Example 1 above) (1 mmol) in toluene (10 mL) is added dropwise to a stirred solution of sodium bis(2-methoxyethoxy)aluminum hydride (2 mmol) in toluene (10 mL) at 0° C. under an inert atmosphere. Stirring is continued at 0° C. and the progress of the reaction is followed by thin layer chromatography (tlc). After the reaction is complete, the reaction mixture is added dropwise to vigorously stirred ice cold water (0.5 mL). Sodium potassium tartrate (10 mL, 0.5 M) is added and the reaction mixture is stirred for several hours. Ether is added to the reaction mixture and the layers are separated. The aqueous layer is further extracted with chloroform. The combined organic extracts are dried (Na$_2$SO$_4$), filtered and concentrated under reduced pressure to give the crude product. The desired compound 22 (where R$^1$=Cl, n=1, and the olefinic bond is trans) is obtained by purification of the crude product with the use of HPLC.

Step 2

A solution of compound 22 (where R$^1$=Cl and n=1) and trifluoroacetic acid (3 mL) in CH$_2$Cl$_2$ (5 mL) is stirred at room temperature. The progress of the reaction is followed by tlc. After the reaction is complete, more CH$_2$Cl$_2$ is added and the solution is washed with aqueous Na$_2$CO$_3$ and with H$_2$O. The organic layer is dried (Na$_2$SO$_4$), filtered and concentrated under reduced pressure to give the crude product. The desired compound of Formula I (structure 23 where R$^1$=Cl, R$^2$=H, n=1, and linked via a trans olefinic bond) is obtained by purification of the crude product with the use of HPLC.

Example 3

Following FIG. 8

Preparation of a Formula I Compound Wherein p is 2, q is 1, and Each L is (S)-2-chloro-5-(2-azetidinylmethoxy)pyridine and the Linker, X, is a cis Ethylenic Bond

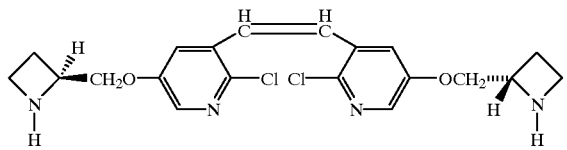

Step 1

A solution of the compound 20 (where R$^1$=Cl and n=1) (1 mmol) prepared as described in Example 1 above in toluene (10 mL) is stirred with palladium-on-charcoal (0.040 g) in a hydrogen atmosphere using a semi-micro hydrogenation apparatus until tlc evidence shows that reaction is complete. The mixture is filtered through Celite® and the filter cake is washed with EtOAc. The filtrate is concentrated under reduced pressure to provide the crude product. The desired compound 22 (where R$^1$=Cl, n=1, and linked via a cis olefinic bond) is obtained by purification of the crude product with the use of HPLC.

Step 2

A solution of the product 22 (where R$^1$=Cl and n=1) and trifluoroacetic acid (3 mL) in CH$_2$Cl$_2$ (5 mL) is stirred at room temperature. The progress of the reaction is followed by tlc. After reaction is complete, more CH$_2$Cl$_2$ is added and the solution is washed with aqueous Na$_2$CO$_3$ and with H$_2$O. The organic layer is dried (Na$_2$SO$_4$), filtered and concentrated under reduced pressure to give the crude product. The desired compound of Formula I (structure 23, where R$^1$=Cl, R$^2$=H, n=1, and linked via a cis olefinic bond) is obtained by purification of the crude product with the use of HPLC.

Example 4

Following FIG. 8

Preparation of a Formula I Compound Wherein p is 2, q is 1, and Each L is (S)-2-chloro-5-(2-azetidinylmethoxy)pyridine and the Linker, X, is an Ethylene Chain

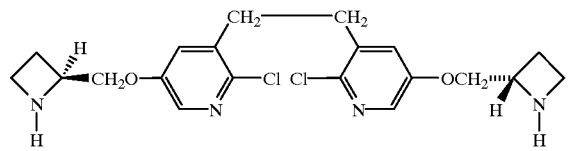

Step 1

A solution of either of compound 20 or 22 (1 mmol) in ethyl acetate (10 mL) is hydrogenated at atmospheric pressure in the presence of 10% palladium-on-carbon until tlc evidence shows that reaction is complete. The mixture is filtered through Celite® and the filter pad is washed thoroughly with ethyl acetate. The combined filtrates are concentrated under reduced pressure to give the crude product. The desired compound 24 (where R$^1$=Cl and n=1) is obtained by purification of the crude product with the use of HPLC.

Step 2

A solution of compound 24 (where R$^1$=Cl and n=1) and trifluoroacetic acid (3 mL) in CH$_2$Cl$_2$ (5 mL) is stirred at room temperature. The progress of the reaction is followed by tlc. After the reaction is complete, more CH$_2$Cl$_2$ is added and the solution is washed with aqueous Na$_2$CO$_3$ and with H$_2$O. The organic layer is dried (Na$_2$SO$_4$), filtered and concentrated under reduced pressure to give the crude product. The desired compound of Formula I (structure 25, where R$^1$=Cl, R$^2$=H, n=1, and linked via an ethylene chain) is obtained by purification of the crude product with the use of HPLC.

(B) Alternately, either of the compounds obtained in Step 2 of Examples 2 and 3 are treated as described in Step 1 of this example to generate directly the desired compound of Formula I (structure 25, where R$^1$=Cl, R$^2$=H, n=1).

Example 5

Figure 9:
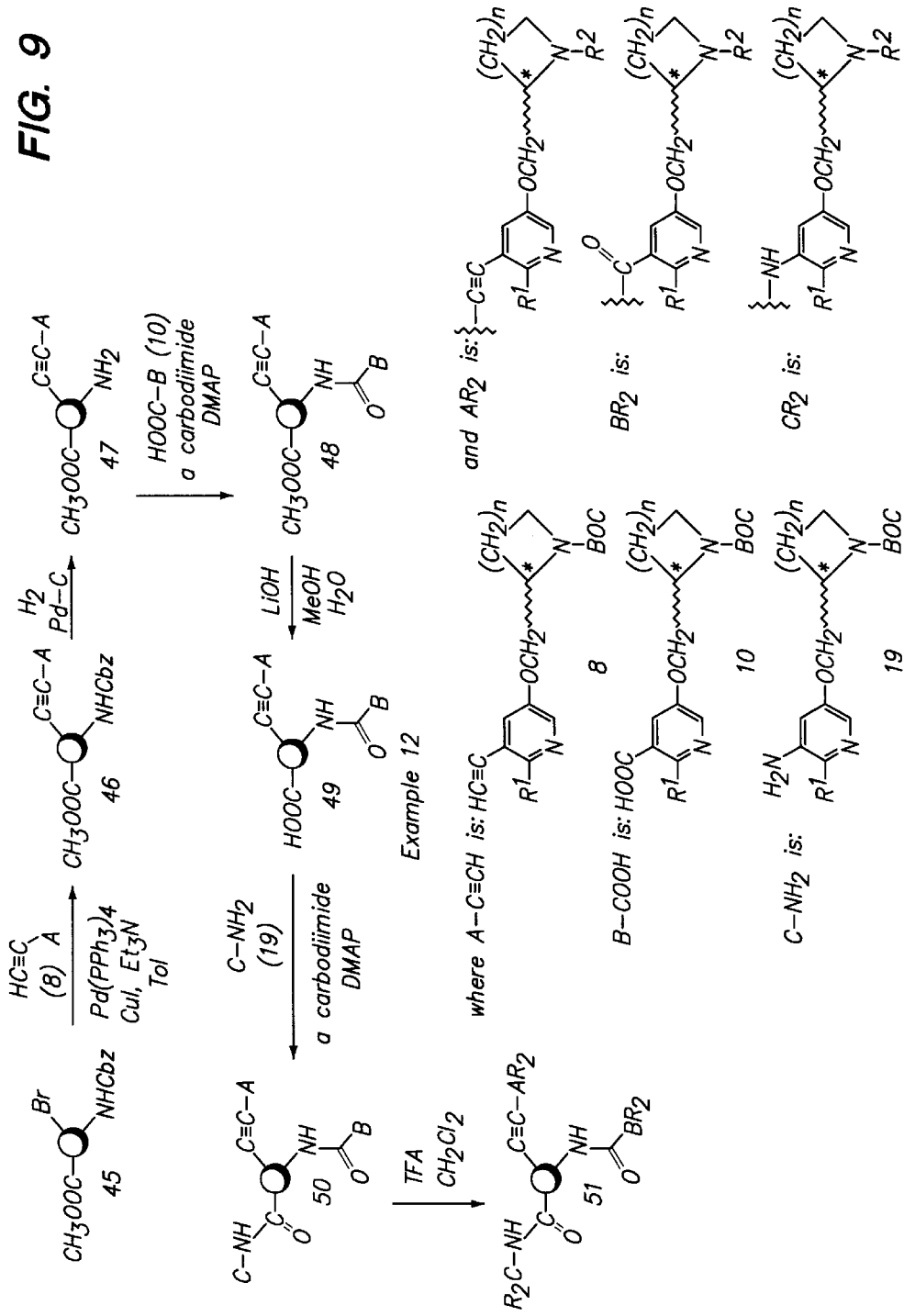

Following FIG. 9

Preparation of a Formula I Compound Wherein p is 2, q is 1, Each L is (S)-2-chloro-5-(2-azetidinylmethoxy)pyridine and the Linker, X, is 1,3-butynyl

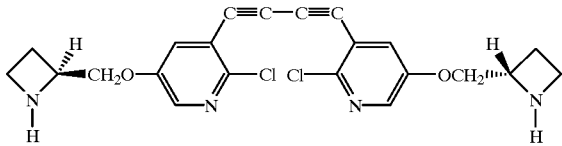

Step 1

A solution of (S)-2-chloro-3-bromo-5-(2-azetidinylmethoxy)pyridine 5 (R$^1$=Cl and n=1) (1 mmol), tetrakis(triphenylphosphine)palladium(0) (100 mg), and triethylamine (0.3 mL) in toluene (10 mL) is stirred with copper (I) iodide (15 mg). The reaction mixture is stirred at 100° C. and the progress of the reaction is followed by thin layer chromatography (tlc). After the reaction is complete, the mixture is cooled, filtered, and the solvent is removed under reduced pressure to give the crude reaction product. The desired compound 26 (where R$^1$=Cl and n=1) is obtained by purification of the crude product with the use of HPLC.

Step 2

A solution of the compound 26 (where R$^1$=Cl and n=1) obtained in the preceding experiment in MeOH is stirred with K$_2$CO$_3$ and the progress of the reaction is followed by tlc. After the reaction is complete, the reaction mixture is filtered and the filtrate is concentrated under reduced pressure to give the crude product. The desired compound 27 (where $R^1$=Cl and n=1) is obtained by purification of the crude product with the use of HPLC.

Step 3

A solution of compound 27 (where $R^1$=Cl and n=1) (1 mmol), (S)-2-chloro-3-bromo-5-(2-azetidinylmethoxy) pyridine 5 ($R^1$=Cl and n=1) (1 mmol), tetrakis (triphenylphosphine)palladium(0) (150 mg), and triethylamine (0.3 mL) in toluene (10 mL) is stirred with copper (I) iodide (20 mg). The mixture is stirred at 100° C. and the progress of the reaction is followed by thin layer chromatography (tlc). After the reaction is complete, the mixture is cooled, filtered, and the solvent is removed under reduced pressure to give the crude reaction product. The desired compound 28 (where $R^1$=Cl and n=1) is obtained by purification of the crude product with the use of HPLC.

Step 4

A solution of compound 28 (where $R^1$=Cl and n=1) and trifluoroacetic acid (3 mL) in $CH_2Cl_2$ (5 mL) is stirred at room temperature. The progress of the reaction is followed by tlc. After the reaction is complete, more $CH_2Cl_2$ is added and the solution is washed with aqueous $Na_2CO_3$ and $H_2O$. The organic layer is dried ($Na_2SO_4$), filtered and concentrated under reduced pressure to give the crude product. The desired compound of Formula I (structure 29, where $R^1$=Cl and $R^2$=H, n=1) is obtained by purification of the crude product with the use of HPLC.

Note that by choice of compounds of structure 5 having $R^1$ and/or n different from each other, compounds of Formula I having two different ligands, L, are prepared.

Example 6

Following FIG. 9

Preparation of a Formula I Compound Wherein p is 2, q is 1, Each L is (s)-2-chloro-5-(2-azetidinylmethoxy)pyridine and the Linker, X, is n-butyl

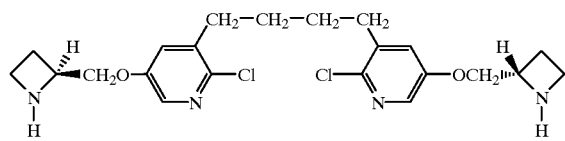

Step 1

A solution of compound 28 (where $R^1$=Cl and n=1) (1 mmol), prepared as described in example 5 above, in ethyl acetate (10 mL) is hydrogenated at atmospheric pressure in the presence of 10% palladium-on-carbon until tlc evidence shows that reaction is complete. The mixture is filtered through Celite® and the filter pad is washed thoroughly with ethyl acetate. The combined filtrates are concentrated under reduced pressure to give the crude product. The desired compound 30 (where $R^1$=Cl and n=1) is obtained by purification of the crude product with the use of HPLC.

Step 2

A solution of compound 30 (where $R^1$=Cl and n=1) and trifluoroacetic acid (3 mL) in $CH_2Cl_2$ (5 mL) is stirred at room temperature. The progress of the reaction is followed by tlc. After the reaction is complete, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 31, where $R^1$=Cl, $R^2$=H, and n=1,) is obtained by purification of the crude product with the use of HPLC.

Alternately, the compound obtained in Step 2 of Example 5 is treated as described in Step 1 of this example to generate directly the desired compound of Formula I (structure 31, where $R^1$=Cl, $R^2$=H, and n=1).

Example 7

Figure 10:
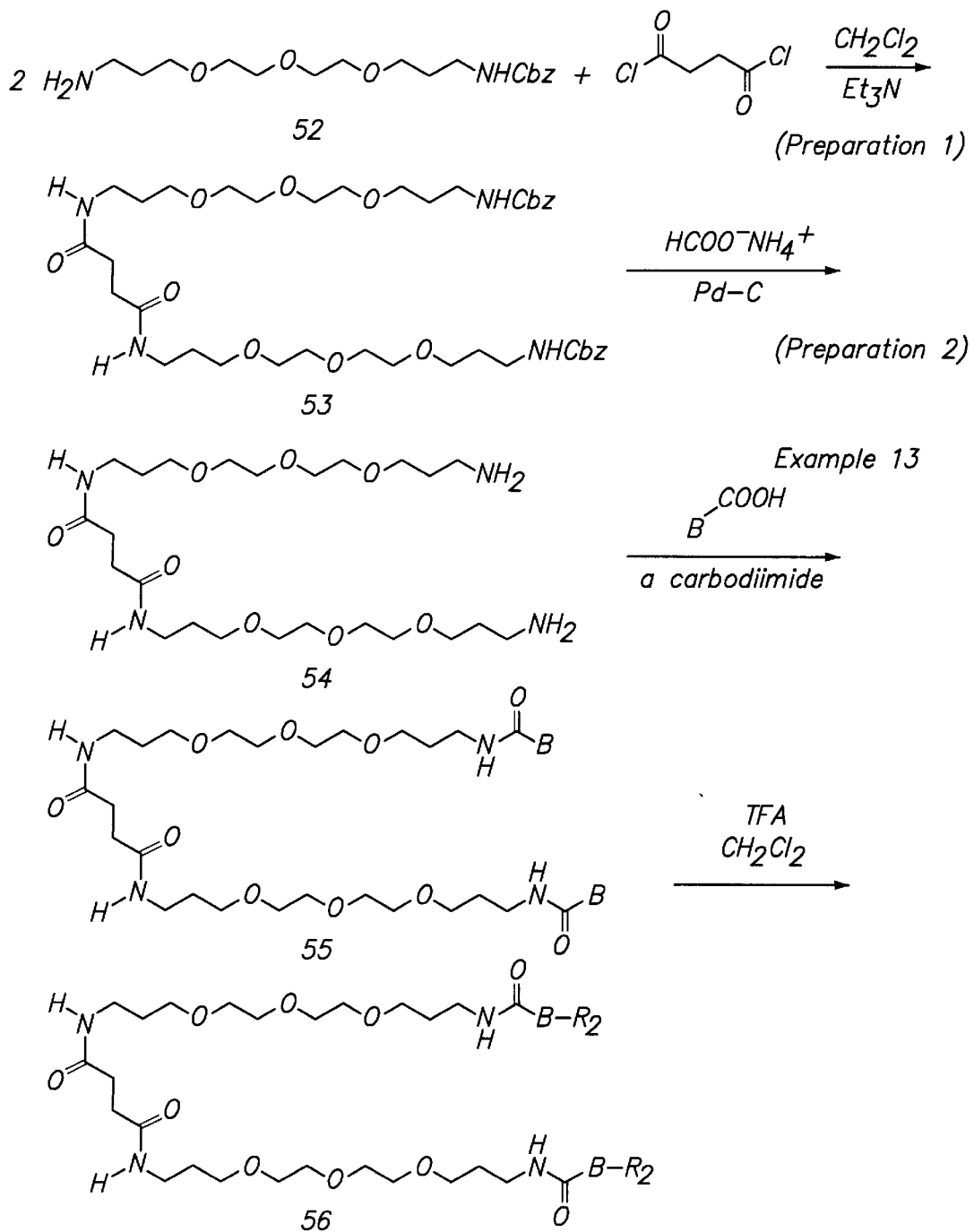

Following FIG. 10

Preparation of a Formula I Compound Wherein p is 2, q is 1, Each L is (S)-2-chloro-5-(2-azetidinylmethoxy)pyridine and the Linker, X, is 1,4-bis-ethynylbenzene

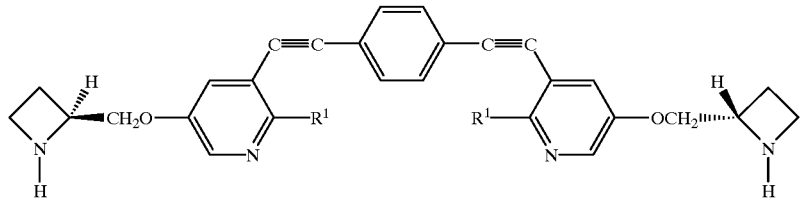

Step 1

A solution of (S)-2-chloro-3-ethynyl-5-(2-azetidinylmethoxy)pyridine 8 ($R^1$=Cl and n=1) (2 mmol), the linker molecule 1,4-diiodobenzene (1 mmol), tetrakis (triphenylphosphine)palladium(0) (150 mg), and triethylamine (0.3 mL) in toluene (10 mL) is stirred with copper (I) iodide (20 mg). The reaction mixture is stirred at 100 ° C. and the progress of the reaction is followed by thin layer chromatography (tlc). After the reaction is complete, the reaction mixture is cooled, filtered, and the solvent is removed under reduced pressure to give the crude reaction product. The desired compound 33 (where $R^1$=Cl and n=1) is obtained by purification of the crude product with the use of HPLC.

Step 2

A solution of compound 33 (where $R^1$=Cl and n=1) and trifluoroacetic acid (3 mL) in $CH_2Cl_2$ (5 mL) is stirred at room temperature. The progress of the reaction is followed by tlc. After the reaction is complete, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 34, where $R^1$=Cl, $R^2$=H, and n=1) is obtained by purification of the crude product with the use of HPLC.

Example 8

Following FIG. 10

Preparation of a Formula I Compound Wherein p is 2, q is 1, Each L is (S)-2-chloro-5-(2-azetidinylmethoxy)pyridine and the Linker, X, is 1,4-bis-ethylenebenzene

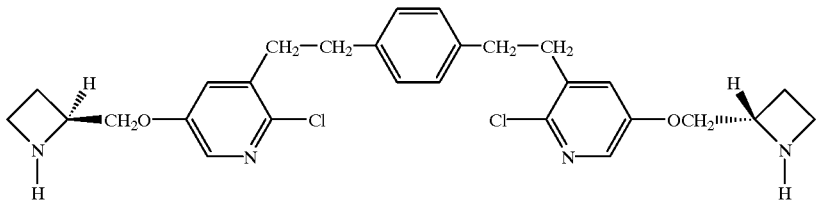

Step 1

A solution of compound 33 (where $R^1$=Cl and n=1) prepared as described in Step 1 of Example 7 (1 mmol) in ethyl acetate (10 mL) is hydrogenated at atmospheric pressure in the presence of 10% palladium-on-carbon until tlc evidence shows that reaction is complete. The reaction mixture is filtered through Celite® and the filter pad is washed thoroughly with ethyl acetate. The combined filtrates are concentrated under reduced pressure to give the crude product. The desired compound 35 (where $R^1$=Cl and n=1) is obtained by purification of the crude product with the use of HPLC.

Step 2

A solution of compound 35 (where $R^1$=Cl and n=1) and trifluoroacetic acid (3 mL) in $CH_2Cl_2$ (5 mL) is stirred at room temperature. The progress of the reaction is followed by tlc. After the reaction is complete, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 36, where $R^1$=Cl, $R^1$=H, and n=1) is obtained by purification of the crude product with the use of HPLC.

Alternately, compound 34 obtained in Step 2 of Example 7 is treated as described in Step 1 of this example to generate directly the desired compound of Formula I (structure 36, where $R^1$=Cl, $R^2$=H, and n=1).

Example 9

Figure 11:
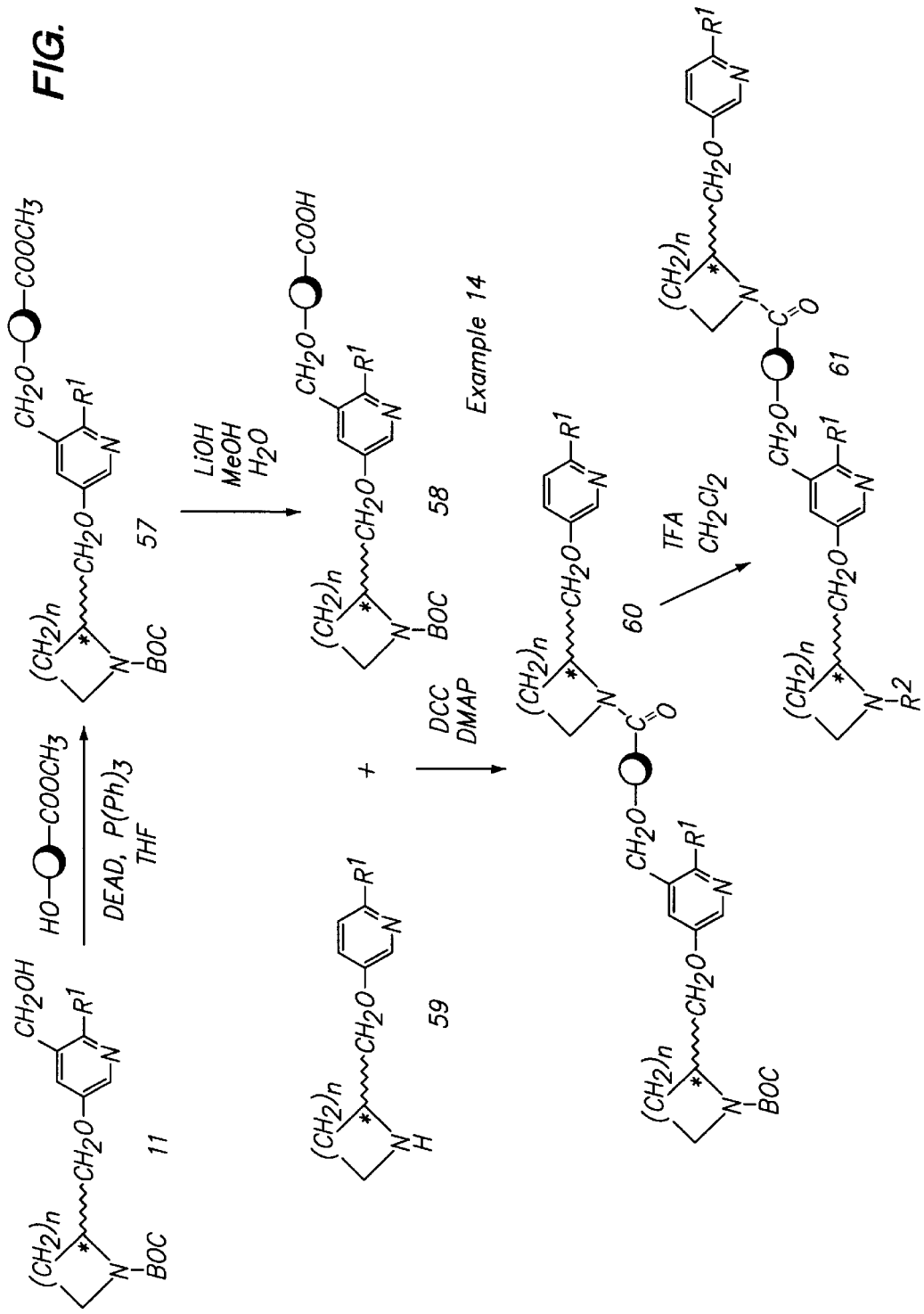

Following FIG. 11

Preparation of a Formula I Compound Wherein p is 2, q is 1, Each L is (S)-2-chloro-5-(2-azetidinylmethoxy)pyridine and the Linker, X, is 1,4-bis-amidomethylbenzene Step 1

A solution of (S)-2-chloro-3-amino-5-(2-azetidinylmethoxy)pyridine 19 ($R^1$=Cl and n=1) (2 mmol) and the linker molecule benzene-1,3-bisacetic acid (1 mmol) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound of Formula I (structure 37, where $R^1$=Cl and n=1) is obtained by purification of the crude product with the use of HPLC.

Step 2

A solution of compound of Formula I (structure 37, where $R^1$=Cl and n=1) and trifluoroacetic acid (3 mL) in $CH_2Cl_2$ (5 mL) is stirred at room temperature. The progress of the reaction is followed by tlc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 38, where $R^1$=Cl, $R^2$=H, and n=1) is obtained by purification of the crude product with the use of HPLC.

Example 10

Following FIG. 11

Preparation of a Formula I Compound Wherein p is 2, q is 1, Each L is (S)-2-chloro-5-(2-azetidinylmethoxy)pyridine and the Linker, X, is 1,4-bis-amidomethylbenzene

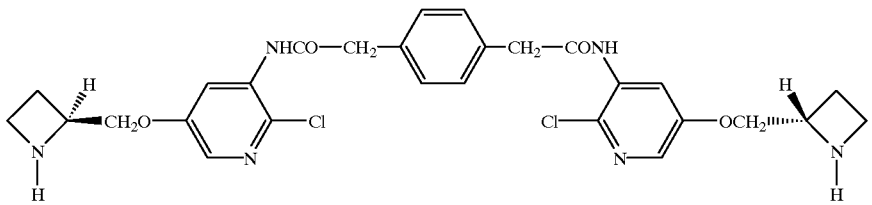

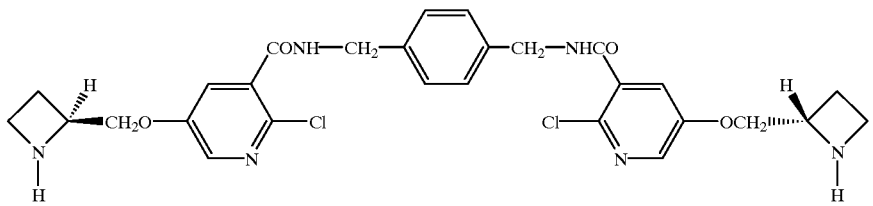

Step 1

A solution of (S)-2-chloro-3-carboxy-5-(2-azetidinylmethoxy)pyridine 10 ($R^1$=Cl and n=1) (2 mmol) and the linker molecule 1,4-bisaminomethylbenzene (1 mmol) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound 39 (where $R^1$=Cl and n=1) is obtained by purification of the crude product with the use of HPLC.

Step 2

A solution of compound 39 (where $R^1$=Cl and n=1) and trifluoroacetic acid (3 mL) in $CH_2Cl_2$ (5 mL) is stirred at room temperature. The progress of the reaction is followed by tlc. After the reaction is complete, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 40, where $R^1$=Cl, $R^2$=H, and n=1) is obtained by purification of the crude product with the use of HPLC.

Example 11

Figure 12:
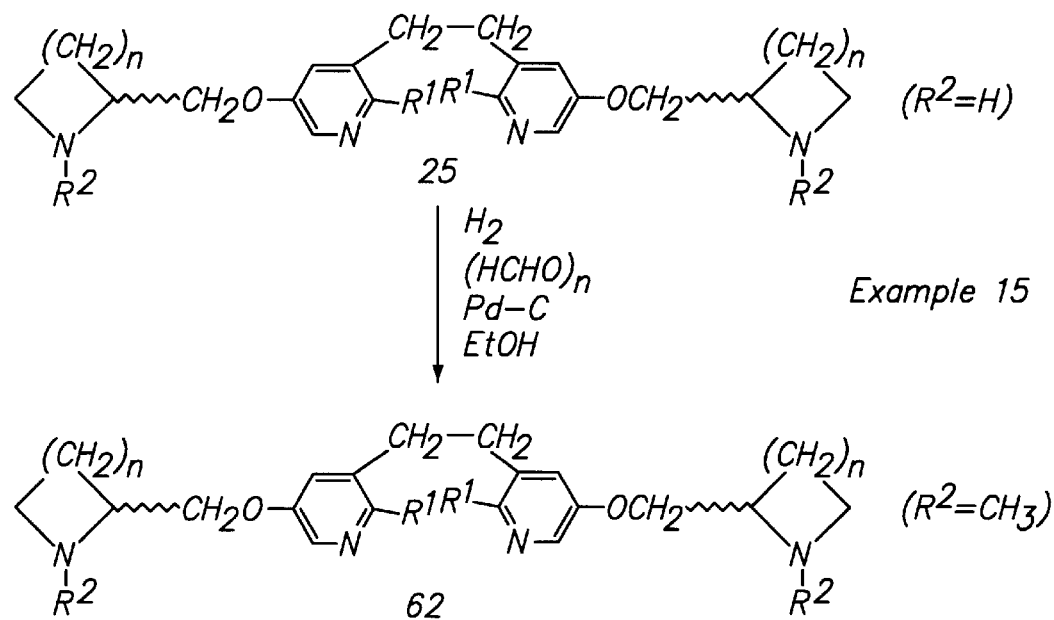

Following FIG. 12

Preparation of a Formula I Compound Wherein p is 2, q is 1, One of the Ligand, L, is (S)-2-chloro-5-(2-azetidinylmethoxy)pyridine, Another Ligand is (S)-2-methyl-5-(2-azetidinylmethoxy)pyridine, and the Linker, X, is —NH—CO—$CH_2$—NH—CO—

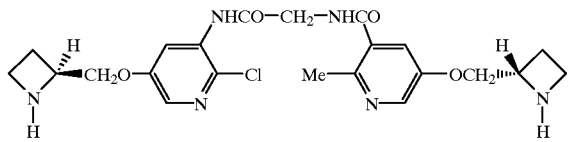

Step 1

A solution of (S)-2-chloro-3-amino-5-(2-azetidinylmethoxy)pyridine 19 ($R^1$=Me and n=1) (2 mmol) and the linker molecule, an N-Cbz glycine (1 mmol) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound 41 (where $R^1$=Me and n=1) is obtained by purification of the crude product with the use of HPLC.

Step 2

Ammonium formate (96 mg, 1.5 mmol) and 10% Pd—C (50 mg) are added to a solution of compound 41 in methanol (3 mL) and THF (2 mL). The reaction mixture is stirred at room temperature and the progress of the reaction is monitored by tlc. After reaction is complete, the reaction mixture is filtered through Celite®, the filter pad is rinsed with EtOAc, and the combined organic layers are washed successively with aqueous $NaHCO_3$ and with half-saturated brine, then filtered and concentrated under reduced pressure to give the crude product. The desired compound 42 (where $R^1$=Me and n=1) is obtained by purification of the crude product with the use of HPLC.

Step 3

Compound 42 and (S)-2-chloro-3-carboxy-5-(2-azetidinylmethoxy)pyridine 10 ($R^1$=Cl and n=1) (1 mmol) are dissolved in methylene chloride (5 mL) and the solution is stirred under argon in a flask equipped with magnetic stirrer and a drying tube. To this solution is added dicyclohexylcarbodiimide (solid, 1 mmol). The progress of the reaction is followed by tlc and after the reaction is complete, the reaction mixture is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound 43 (where n=1) is obtained by purification of the crude product with the use of HPLC.

Step 4

A solution of compound 43 (where n=1) and trifluoroacetic acid (3 mL) in $CH_2Cl_2$ (5 mL) is stirred at room temperature. The progress of the reaction is followed by tlc. After the reaction is complete, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 44, where $R^2$=H and n=1) is obtained by purification of the crude product with the use of HPLC.

Example 12

Following FIG. 13

Preparation of a Formula I Compound Wherein p is 3, q is 1, Ligand, $L_1$, is (S)-2-chloro-5-(2-azetidinylmethoxy)pyridine, Ligands, $L_2$ and $L_3$ are (S)-2-methyl-5-(2-azetidinylmethoxy)pyridine, and the Linker, X, is —NH—CO—CH(—C≡C—)—NH—CO—

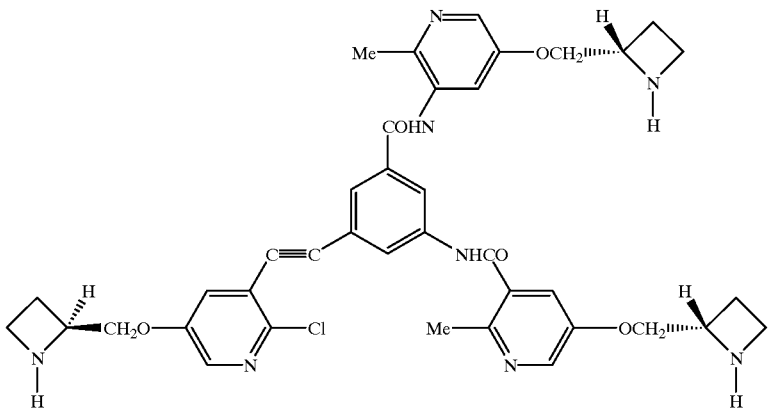

Step 1

A solution of (S)-2-chloro-3-ethynyl-5-(2-azetidinylmethoxy)pyridine 8 ($R^1$=H and n=1) (1 mmol), the linker molecule 1-iodo-3-(N-benzyloxycarbonyl)amino-5-methoxycarbononylbenzene 45 (1 mmol), tetrakis(triphenylphosphine)palladium(0) (150 mg), and triethylamine (0.3 mL) in toluene (10 mL) is stirred with copper (I) iodide (20 mg). The reaction mixture is stirred at 100 °C. and the progress of the reaction is followed by thin layer chromatography (tlc). After the reaction is complete, the reaction mixture is cooled, filtered, and the solvent is removed under reduced pressure to give the crude reaction product. The desired compound 46 (where $R^1$=H, $R^2$=BOC, and n=1) is obtained by purification of the crude product with the use of HPLC.

Step 2

Ammonium formate (96 mg, 1.5 mmol) and 10% Pd—C (50 mg) are added to a solution of the compound 46 in methanol (3 mL) and THF (2 mL). The reaction mixture is stirred at room temperature and the progress of the reaction is monitored by tlc. After reaction is complete, the mixture is filtered through Celite®, the filter pad is rinsed with EtOAc, the combined organic layers are washed successively with aqueous $NaHCO_3$ and with half-saturated brine, then filtered and concentrated under reduced pressure to give the crude product. The desired compound 47 (where $R^1$=H and n=1) is obtained by purification of the crude product with the use of HPLC.

Step 3

The product from the preceding reaction and (S)-²-chloro-3-carboxy-5-(2-axetidinylmethoxy)pyridine (structure 10, $R^1$=Cl, n=1) (1 mmol) are dissolved in methylene chloride (5 mL) and the solution is stirred under argon in a flask equipped with magnetic stirrer and a drying tube. To this solution is added dicyclohexylcarbodiimide (solid, 1 mmol). The progress of the reaction is followed by tlc and after the reaction is complete, the reaction mixture is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound 48 (where n=1) is obtained by purification of the crude product with the use of HPLC.

Step 4

A mixture of compound 48 and lithium hydroxide (100 mmols) in methanol (6 mL) and water (2mL) is stirred at room temperature. The reaction is followed by thin layer chromatography. After reaction occurs, the pH of the solution is adjusted to 7 by the addition of dilute aqueous hydrochloric acid. The solvent is removed by lyophilization and the dry, crude product 49 (where n=1) is used directly in the next reaction.

Step 5

A solution of (S)-2-chloro-3-amino-5-(2-azetidinylmethoxy)pyridine 19 ($R^1$=Me and n=1) (2 mmol) and compound 49 in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after the reaction is complete; the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound 50 (where $R^1$=H and n=1) is obtained by purification of the crude product with the use of HPLC.

Step 6

A solution of compound 50 and trifluoroacetic acid (3 mL) in $CH_2Cl_2$ (5 mL) is stirred at room temperature. The progress of the reaction is followed by tlc. After the reaction is complete, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 51, where $R^2$=H and n=1) is obtained by purification of the crude product with the use of HPLC.

Example 13

Following FIG. 14

Preparation of a Formula I Compound Wherein p is 2, q is 1, Each L is (S)-2-chloro-3-carboxy-5-(2-azetidinylmethoxy)pyridine and the Linker, X, is —CO—NH—$(CH_2O)_3$—$(CH_2)_3$—NH—CO—$(CH_2)_2$—NH—CO—$(CH_2)_3$—$(OCH_2)_3$—$(CH_2)_3$—NH—CO—

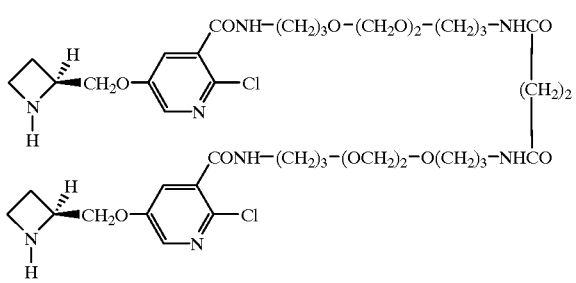

Step 1

A solution of the compound 52 (10 mmol) in CH$_2$Cl$_2$ (10 mL) is added dropwise to a cooled, stirred solution of Step 4

A solution of compound 55 (where R$^1$=Cl and n=1) and trifluoroacetic acid (3 mL) in CH$_2$Cl$_2$ (5 mL) is stirred at room temperature. The progress of the reaction is followed by tlc. After the reaction is complete, more CH$_2$Cl$_2$ is added and the solution is washed with aqueous Na$_2$CO$_3$ and with H$_2$O. The organic layer is dried (Na$_2$SO$_4$), filtered and concentrated under reduced pressure to give the crude product. The desired compound of Formula I (structure 56, where R$^1$=Cl, R$^2$=H, and n=1) is obtained by purification of the crude product with the use of HPLC.

Example 14

Following FIG. 15

Preparation of a Formula I Compound Wherein p is 2, q is 1, Each linker, L, is (S)-2-chloro-5-(2-azetidinylmethoxy)pyridine and the Linker, X, 1,4-CH$_2$—O-phenylene-CO—

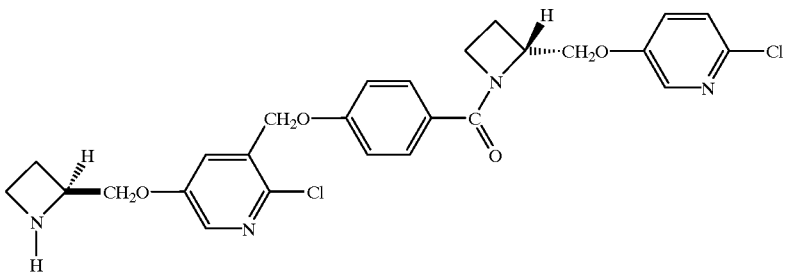

succinoyl chloride in CH$_2$Cl$_2$ (20 mL) and triethyl amine (1 mL). The reaction mixture is allowed to come to room temperature and stirring is continued. Saturated aqueous potassium hydrogen sulfate is added carefully and the mixture stirred briefly. The layer are separated and the organic layer is washed with brine, dried (Na$_2$SO$_4$), filtered and concentrated under reduced pressure to give the crude product. The crude product is purified by the use of HPLC giving the desired pure 53.

Step 2

Ammonium formate (96 mg, 1.5 mmol) and 10% Pd—C (50 mg) are added to a solution of the compound (1 mmol) obtained in the preceding reaction in methanol (5 mL) and THF (4 mL). The reaction mixture is stirred at room temperature and the progress of the reaction is monitored by tlc. After the reaction is complete, the mixture is filtered through Celite®, the filter pad is rinsed with EtOAc, the combined organic layers are washed successively with aqueous NaHCO$_3$ and with half-saturated brine, then filtered and concentrated under reduced pressure to give the crude product 54.

Step 3

A solution of (S)-2-chloro-3-carboxy-5-(2-azetidinylmethoxy)pyridine 10 (where R$^1$=Cl and n=1) (2 mmol) and the linker molecule, compound 54 (1 mmol) in CH$_2$Cl$_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after the reaction is complete, the reaction solution is quenched in water, aqueous sodium bicarbonate is added and the aqueous mixture is extracted with methylene chloride. The organic layer is washed with aqueous Na$_2$CO$_3$ and with H$_2$O, dried (Na$_2$SO$_4$), filtered and concentrated under reduced pressure to give the crude product. The desired compound 55 (where R$^1$=Cl and n=1) is obtained by purification of the crude product with the use of HPLC.

Step 1

Diethyl azodicarboxylate (1 mmol) is added dropwise via a syringe to a stirred solution of triphenylphosphine (1 mmol) in THF (5 mL) at room temperature. To this is added a solution of (S)-2-chloro-3-hydroxymethyl-5-(2-azetidinylmethoxy)pyridine 11 (where R$^1$=Me and n=1) (1 mmol) and the linker molecule, p-methoxycarbonylphenol (1 mmol) in THF (1 mL). The resulting solution is stirred at RT and the progress of the reaction is followed by tlc. After the reaction is complete, solvent is removed by evaporation under reduced pressure and the residue is purified by HPLC, giving the desired compound 57 (where R$^1$=Cl and n=1).

Step 2

A solution of compound 57 and lithium hydroxide (100 mmols) in methanol (6 mL) and water (2 mL) is stirred at room temperature. The reaction is followed by thin layer chromatography. After reaction occurs, the pH of the solution is adjusted to 7 by the addition of dilute aqueous hydrochloric acid. The solvent is removed by lyophilization and the dry, crude product 58 (where R$^1$=Cl and n=1) is used directly in the next reaction.

Step 3

A solution of (S)-2-chloro-5-(2-azetidinylmethoxy)pyridine 59 (where n=1) (1 mmol) and compound 58 in CH$_2$Cl$_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after the reaction is complete, the reaction solution is quenched in water, aqueous sodium bicarbonate is added and the aqueous mixture is extracted with methylene chloride. The organic layer is washed with aqueous Na$_2$CO$_3$ and with H$_2$O, dried (Na$_2$SO$_4$), filtered and concentrated under reduced pressure to give the crude product. The desired compound 60 (where R$^1$=Cl and n=1) is obtained by purification of the crude product with the use of HPLC.

Step 4

A solution of compound 60 (where $R^1$=Cl and n=1) and trifluoroacetic acid (3 mL) in $CH_2Cl_2$ (5 mL) is stirred at room temperature. The progress of the reaction is followed by tlc. After the reaction is complete, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 61, where $R^1$=Cl, $R^2$=H, and n=1) is obtained by purification of the crude product with the use of HPLC.

Example 15

Following FIG. 16
Preparation of a Formula I Compound Wherein p is 2, q is 1, and Each L is (S)-2-chloro-5-(N-methyl-2-azetidinylmethoxy)pyridine and the Linker, X, is an Ethylene Chain

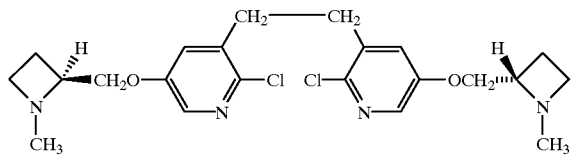

A solution of the compound 25 prepared as described in Example 4 (where $R^1$=Cl, $R^2$=H, and n=1) (1 mmol) and paraformaldehyde (5 mmol) in ethanol (5 mL) is stirred with 10% Pd—C (20 mg) under a hydrogen atmosphere. The progress of the reaction is followed by tlc. After the reaction is complete, the mixture is filtered through Celite®, the filter pad is washed with ethanol, and the filtrates are concentrated under reduced pressure. The desired compound of Formula I (structure 62, where $R^1$=Cl, $R^2$=$CH_3$, and n=1) is obtained by purification of the crude product with the use of HPLC.

In similar manner, by replacing a compound of Formula I used in the above example with other compounds of Formula I, where $R^2$=H, other compounds of Formula I, where $R^2$=$CH_3$, are prepared.

Example 16

This example illustrates the preparation of a representative pharmaceutical formulation for oral administration containing a multibinding compound of the invention.

| Ingredients | Quantity per tablet, mgs. |
|---|---|
| Active Compound | 200 |
| Lactose, spray-dried | 148 |
| Magnesium stearate | 2 |

The above ingredients are mixed and introduced into a hard-shell gelatin capsule. Other multibinding compounds of the invention can be used as the active compound in the preparation of the orally administrable formulations of this example.

Example 17

This example illustrates the preparation of another representative pharmaceutical formulation for oral administration containing a multibinding compound of the invention.

| Ingredients | Quantity per tablet, mgs. |
|---|---|
| Active Compound | 400 |
| Cornstarch | 50 |
| Lactose | 145 |
| Magnesium stearate | 5 |

The above ingredients are mixed intimately and pressed into single scored tablets. Other multibinding compounds of the invention can be used as the active compound in the preparation of the orally administrable formulations of this example.

Example 18

This example illustrates the preparation of a representative pharmaceutical formulation containing a multibinding compound of the invention An oral suspension is prepared having the following composition.

| Ingredients | |
|---|---|
| Active Compound | 1.0 g |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

Other multibinding compounds of the invention can be used as the active compound in the preparation of the orally administrable formulations of this example.

Example 19

This example illustrates the preparation of a representative pharmaceutical formulation containing a multibinding compound of the invention.

An injectable preparation buffered to a pH of 4 is prepared having the following composition:

| Ingredients | |
|---|---|
| Active Compound | 0.2 g |
| Sodium Acetate Buffer Solution (0.4 M) | 2.0 ml |
| HCL (1N) | q.s. to pH 4 |
| Water (distilled, sterile) | q.s. to 20 ml |

Other multibinding compounds of the invention can be used as the active compound in the preparation of the injectable formulations of this example.

Example 20

This example illustrates the preparation of a representative pharmaceutical formulation for injection containing a multibinding compound of the invention.

A reconstituted solution is prepared by adding 20 ml of sterile water to 1 g of the compound of Formula I. Before use, the solution is then diluted with 200 ml of an intravenous fluid that is compatible with the compound of Formula I. Such fluids are chosen from 5% dextrose solution, 0.9% sodium chloride, or a mixture of 5% dextrose and 0.9% sodium chloride. Other examples are lactated Ringer's injection, lactated Ringer's plus 5% dextrose injection, Normosol-M and 5% dextrose, Isolyte E, and acylated Ringer's injection.

Other multibinding compounds of the invention can be used as the active compound in the preparation of the injectable formulations of this example.

Example 21

This example illustrates the preparation of a representative pharmaceutical formulation for topical application containing a multibinding compound of the invention.

| Ingredients | grams |
| --- | --- |
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Other multibinding compounds of the invention can be used as the active compound in the preparation of topical formulations of this example.

Example 22

This example illustrates the preparation of a representative pharmaceutical formulation containing a multibinding compound of the invention.

A suppository totaling 2.5 grams is prepared having the following composition:

| Ingredients | |
| --- | --- |
| Active Compound | 500 mg |
| Witepsol H-15* | balance |

(*triglycerides of saturated vegetable fatty acid; a product of Riches-Nelson, Inc., New York, N.Y.)

Other multibinding compounds of the invention can be used as the active compound in the preparation of the suppository formulation of this example.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed:

1. A multibinding compound of the formula:

$(L)_p X_q$   Formula I in which L is a compound of formula (a) that may be the same or different at each occurrence:

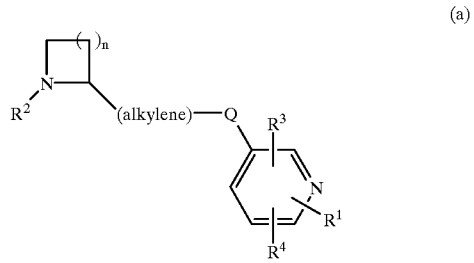

(a)

in which:

n is an integer of 1–3;

$R^1$ is hydrogen, halo, cyano, haloalkyl, alkoxy, alkyl, or a covalent bond connecting the ligand to a linker;

$R^2$ is hydrogen, alkyl, or a covalent bond connecting the ligand to a linker;

$R^3$ is hydrogen, halo, or a covalent bond connecting the ligand to a linker; and $R^4$ is hydrogen, halo, alkyl, alkenyl, alkynyl, nitro, alkoxy, or a covalent bond connecting the ligand to a linker;

Q is —O—, —$NR^5$— in which $R^5$ is hydrogen, alkyl, or a covalent bond connecting the ligand to a linker), or —$S(O)_m$—, in which m is 0 to 2;

or a pharmaceutically acceptable salt or prodrug thereof;

provided that at least one of $R^1$, $R^2$, $R^3$, and $R^4$ is a covalent bond connecting the ligand to a linker;

X is a linker that may be the same or different at each occurrence;

p is an integer of 2–10; and q is an integer of 1–20, each of said ligands compromising a ligand domain capable of binding to an nAChR receptor, or a salt thereof.

2. The compound of claim 1 wherein q is less than p.

3. The compound of claim 2 wherein each ligand L is a compound of formula (a):

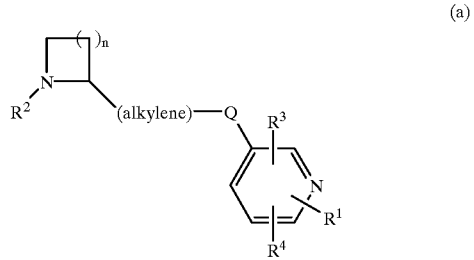

(a)

in which:

n is an integer of 1–3;

$R^1$ is hydrogen, halo, cyano, haloalkyl, alkoxy, alkyl, or a covalent bond connecting the ligand to a linker;

$R^2$ is hydrogen, alkyl, or a covalent bond connecting the ligand to a linker;

R³ is hydrogen, halo, or a covalent bond connecting the ligand to a linker; and

R⁴ is hydrogen, halo, alkyl, alkenyl, alkynyl, nitro, alkoxy, or a covalent bond connecting the ligand to a linker;

Q is —O—, —NR⁵— in which R⁵ is hydrogen, alkyl, or a covalent bond connecting the ligand to a linker), or —S(O)$_m$—, in which m is 0 to 2;

or a pharmaceutically acceptable salt or prodrug thereof; provided that at least one of R¹, R², R³, and R⁴ is a covalent bond connecting the ligand to a linker.

4. The multibinding compound of claim 3, wherein the linker is represented by the formula:

—X'—Z'—(Y'—Z")$_m$—Y"—Z'—X'— in which:

m is an integer of 0–20;

X' at each separate occurrence is —O—, —S—, —S(O)—, —S(O)₂—, —NR— (where R is as defined below), —C(O)—, or a covalent bond;

Z' and Z" at each separate occurrence are alkylene, cycloalkylene, alkenylene, alkynylene, arylene, heteroarylene, heterocycloalkylene, or a covalent bond;

Y' and Y" at each separate occurrence are:

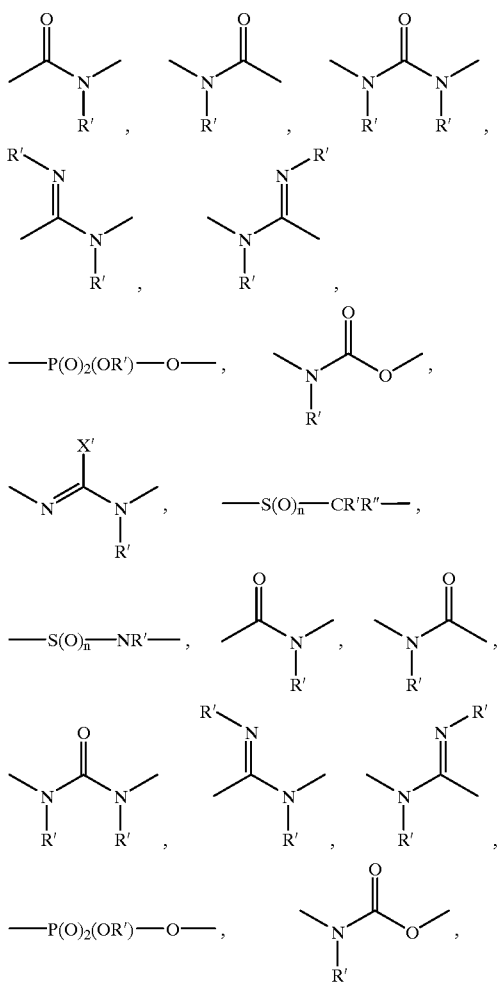

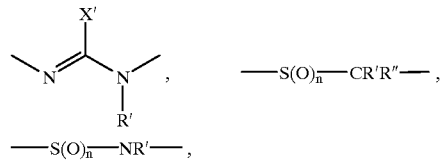

—O—Z'—O—, —N(R)—Z'—N(R), —S—S—, or a covalent bond; in which:

n is 0, 1 or 2; and

R, R' and R" at each separate occurrence are chosen from hydrogen, alkyl, cycloalkyl, alkenyl, cycloalkenyl, alkynyl, aryl, heteroaryl, and heterocyclo.

5. A bivalent multibinding compound of Formula (II):

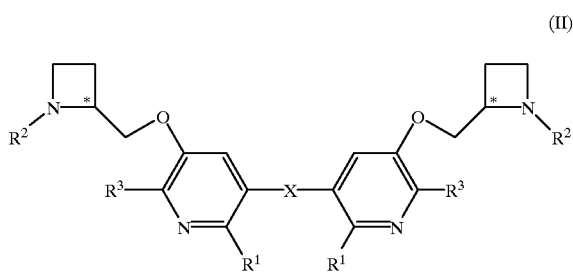

(II)

wherein:

X is a linker;

R¹ is hydrogen, fluoro, bromo, chloro, cyano, —CHF₂, —OMe, —CH₂F, or C1–2-alkyl;

R² is hydrogen or alkyl;

R³ is hydrogen, fluoro, or chloro; and the stereochemistry at *C is R.

6. The compound of claim 5 wherein:

R¹ is hydrogen, methyl, chloro, or bromo;

R² is hydrogen; and

R³ is hydrogen.

7. The compound of claim 6 wherein:

R¹ is chloro or bromo.

8. The compound of claim 7, wherein the linker is represented by the formula:

—X'—Z'—(Y'—Z")$_m$—Y"—Z'—X'— in which:

m is an integer of 0–20;

X' at each separate occurrence is —O—, —S—, —S(O)—, —S(O)₂—, —NR— (where R is as defined below), —C(O)—, or a covalent bond;

Z' and Z" at each separate occurrence are alkylene, cycloalkylene, alkenylene, alkynylene, arylene, heteroarylene, heterocycloalkylene, or a covalent bond;

Y' and Y" at each separate occurrence are;

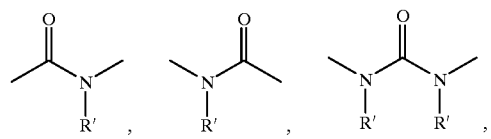

-continued

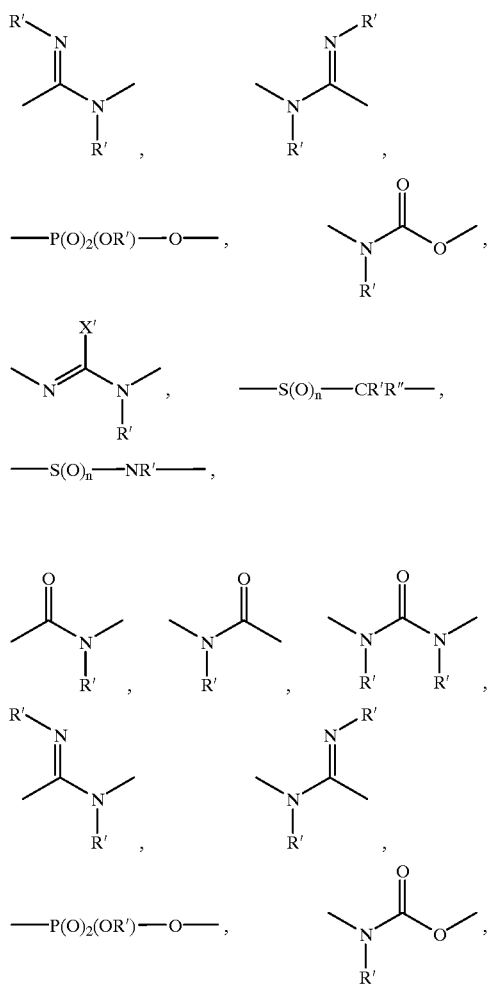

-continued

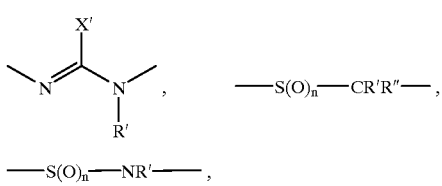

—O—Z'—O—, —N(R)—Z'—N(R), —S—S—, or a covalent bond; in which:

n is 0, 1 or 2; and

R, R' and R" at each separate occurrence are chosen from hydrogen, alkyl, cycloalkyl, alkenyl, cycloalkenyl, alkynyl, aryl, heteroaryl, and heterocyclo.

9. A method for treating a pathologic condition which is alleviated by treatment with an nAChR modulator, comprising administering to a subject in need of such treatment a therapeutically effective amount of a compound of claim 1, which may be the same or different, covalently connected by a linker or linkers, which may be the same or different, each of said ligands comprising a ligand domain capable of binding to an nAChR receptor.

10. A pharmaceutical composition comprising a therapeutically effective amount of a compound of claim 1, which may be the same or different, covalently connected by a linker or linkers, which may be the same or different, each of said ligands compromising a ligand domain capable of binding to an nAChR receptor, admixed with at least one pharmaceutically acceptable excipient.

\* \* \* \* \*